United States Patent
Ho et al.

(10) Patent No.: US 11,103,460 B2
(45) Date of Patent: Aug. 31, 2021

(54) FABRICATION METHODS FOR NANODELIVERY SYSTEMS FOR LONG TERM CONTROLLED DELIVERY OF ACTIVE PHARMACEUTICAL INGREDIENTS

(71) Applicant: BOARD OF REGENTS, THE UNIVERSITY OF TEXAS SYSTEM, Austin, TX (US)

(72) Inventors: Paul S. Ho, Austin, TX (US); Junjun Liu, Austin, TX (US); Tengfei Jiang, Austin, TX (US); Salomon A. Stavchansky, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 124 days.

(21) Appl. No.: 16/056,501

(22) Filed: Aug. 6, 2018

(65) Prior Publication Data

US 2019/0038565 A1    Feb. 7, 2019

Related U.S. Application Data

(60) Provisional application No. 62/542,001, filed on Aug. 7, 2017.

(51) Int. Cl.
*A61K 9/48* (2006.01)
*G03F 7/20* (2006.01)
*G03F 7/16* (2006.01)

(52) U.S. Cl.
CPC .......... *A61K 9/4808* (2013.01); *A61K 9/4833* (2013.01); *G03F 7/16* (2013.01); *G03F 7/2053* (2013.01); *G03F 7/2059* (2013.01); *G03F 7/2065* (2013.01)

(58) Field of Classification Search
None
See application file for complete search history.

(56) References Cited

U.S. PATENT DOCUMENTS

| | | | |
|---|---|---|---|
| 3,854,480 A | 12/1974 | Zaffaroni | |
| 3,948,254 A | 4/1976 | Zaffaroni | |
| 4,014,355 A | 3/1977 | DiMatteo et al. | |
| 4,260,736 A | 4/1981 | Asano et al. | |
| 4,283,394 A | 8/1981 | West et al. | |
| 5,378,475 A | 1/1995 | Smith et al. | |
| 5,902,598 A | 5/1999 | Chen et al. | |
| 5,935,597 A | 8/1999 | Visser | |
| 5,989,581 A | 11/1999 | Groenewegen | |
| 6,039,975 A | 3/2000 | Shah et al. | |
| 6,051,576 A | 4/2000 | Ashton et al. | |
| 9,005,649 B2 | 4/2015 | Ho et al. | |
| 2004/0009222 A1 | 1/2004 | Chou et al. | |
| 2012/0130300 A1 | 5/2012 | Stavchansky et al. | |
| 2012/0177716 A1* | 7/2012 | Ho ............................ A61P 1/04 424/423 |

* cited by examiner

*Primary Examiner* — Dominic Lazaro
(74) *Attorney, Agent, or Firm* — Parker Highlander PLLC

(57) ABSTRACT

Embodiments of the present disclosure include devices, and methods of making such devices, for delivery of one or more active agents with short or long zero-order release kinetics. Embodiments also include implantable or injectable drug delivery systems capable of controlled release over long periods of time for therapeutic agents.

18 Claims, 12 Drawing Sheets

FABRICATION METHODS FOR NANODELIVERY SYSTEMS FOR LONG TERM CONTROLLED DELIVERY OF ACTIVE PHARMACEUTICAL INGREDIENTS

CROSS-REFERENCE TO RELATED APPLICATIONS

This application claims priority to U.S. Provisional Patent Application Ser. No. 62/542,001, filed Aug. 7, 2017, the entire contents of which are incorporated herein by reference.

BACKGROUND INFORMATION

A number of implantable drug delivery devices have been suggested to be capable of delivering an active agent to the body lumen. Some inherent advantages of implanted drug delivery systems over other more convenient drug administration routes, such as oral and sublingual, are mainly related to the more predictable and uniform bioavailability of various drugs when bypassing the digestive tract, and related to localized drug delivery close to the targeted sites without much a systemic effect. This significantly improves efficacy and compliance, especially, in the elderly patient population and in the treatment of drug addiction. In addition, it significantly minimizes potential adverse events.

In many configurations of such drug delivery systems, the drug is often stored in a depot, and the dispensing channel(s) is narrow enough to restrict the drug-release rate so as to maintain a relatively steady zero order rate of drug delivery over an extended period of time. This significantly mitigates the first pass effect and makes control over the delivery kinetics possible. As demonstrated in our previous publications and disclosures, the drug release rate from such a drug delivery device can be directly controlled by the number of perforations, the dimensions of the perforations, the size of the depot, the type of drug and the drug loading.

However, precision dimensional control in the fabrication process of these drug delivery devices can be very challenging in high volume production. Variation in the geometric configurations of the device alone can result in variation of the release rate, and even bigger deviation from the design specifications can cause more dramatical change to the delivery kinetics, for example, going from an intended zero-order kinetics to a first-order or second-order delivery kinetics. Surface topography and rough edge profile can not only affect the release rate, but also lead to preferential tissue response and faster clogging of the dispensing channels. Such problems can have adverse effects on the control over the drug delivery kinetics, thereby resulting in unpredictable drug profile in the plasma and poor therapeutic benefits.

For example, a popular drug delivery device is a drug eluting stent. Stents are mesh-like steel or plastic tubes that are used to open up a clogged atherosclerotic coronary artery or a blood vessel undergoing stenosis. A drug may be attached onto, or impregnated into, the stent that is believed to prevent re-clogging or restenosis a blood vessel. However, the initial release of the drug may be very rapid releasing twenty to forty percent of the total drug in a single day. Such high concentrations of the drug have been reported to result in cytotoxicity at the targeted site.

Existing fabrication techniques for such delivery devices have difficulties in maintaining dimensional and profile control of critical features (e.g. apertures configured to release the agent) in a cost effective manner suitable for large volume production of the devices. For example, it can be difficult in aligning random polymeric structures for patterning. In addition, it can be difficult to transfer a pattern accurately from a mask to a flexible substrate. The cost of using a sequential laser drilling or assembly processes with micron-scale precision can be prohibitively high.

In conventional fabrication processes of such drug delivery devices, the methods of opening apertures in the enclosure often utilize laser drilling. This can create control issues since apertures in the enclosure must be individually drilled. In addition, conventional techniques such as laser drilling use a thermal process to manufacture the apertures, which can make it difficult to control the edge profile. This can further increase difficulty in controlling the release rate of an agent via the apertures. Limited by the wavelength of the laser used, the use of laser drilling cannot be extended to apertures smaller than 10 µm. The sequential laser drilling process can become very expensive when a large number of apertures have to be opened.

Adding to the complexity of the fabrication process, and also one critical challenge that any implantable device has to face, is the biocompatibility of the devices. The in vivo functionality and durability of any implantable device may be compromised by the host response to the foreign implanted materials. There are known approaches to overcoming the in vivo instability of implantable devices, such as (a) biocompatible material coatings, (b) steroidal and nonsteroidal anti-inflammatory drugs, and (c) angiogenic drugs. However, it would be safer and more convenient to make the device completely out of biocompatible materials and use a fabrication process that only utilizes benign processing technologies, i.e., a process that doesn't utilize species or leave behind residues that are not biocompatible after a standard sterilization finishing step. Unfortunately, many biocompatible materials are compliant polymers and for ease of implant, the shape of the depot can be irregular. These features bring new challenges to dimensional control during the fabrication process.

The technological advancements brought by the semiconductor industry and nanotechnology in nano-scale and micro-scale patterning have greatly expanded our capabilities in the design and fabrication of such implantable drug delivery devices. However, direct patterning of compliant, irregularly shaped substrate has always been a challenge due to the difficulties in pattern registry and the large surface height variation. The limited depth of focus of typical precision lithography tools may not allow accurate pattern definition in high volume manufacturing.

Many inventions have attempted to work around this challenge by making it an assembly process: the portion that requires precision patterning is made separately on a more rigid and planar substrate, such as silicon or glass support, and then transferred and assembled with the rest of the system. Such an assembly process, be it innovative, is difficult or not economical to implement in actual production. It simply shifts the burden from patterning to packaging. The alignment of the precision patterned part with the rest of the system takes time and special tooling, leading to much reduced throughput and increased defectivity. More importantly, both silicon and glass are not considered biocompatible. That further adds to the process complexity—as it is imperative to have an additional conformal biocompatible coating to insulate the precision patterned components from the body fluids, which is not always possible. For example, silicon-based precision apertures have to have the inside walls of the dispensing channels completely coated with a reliable biocompatible overcoating. Such conformal coating processes can be very difficult and may put strong constraints on the dimensions and the cross-sectional profile of the apertures.

Furthermore, an estimated 2.4 million people abuse opioids including 586,000 abusing heroin in the US in 2014. The deaths caused by drug overdose (hydrocodone, oxycodone, morphine, codeine, heroin and others) has exceeded the total number of deaths due to traffic accidents, reaching 47,000 in 2014. According to the last available government survey, the economic cost of drug abuse in the United States was estimated at $193 billion in 2007, including $120 billion in lost productivity, $11 billion in healthcare costs—for drug treatment and drug-related medical consequences, and $61 billion in criminal justice costs.

The advent of cheap but deadly potent synthetic opioids, such as fentanyl (30 to 50 times more powerful than heroin) and carfentanil (100 times more powerful than heroin), has pushed the United States' drug addiction crisis to new levels. Drug overdose makes headlines of news reports almost every day. As illicit drug manufacturing and distribution becomes more decentralized, the access barrier enforced by law has become less effective to prevent illicit opioids, especially these synthetic opioids from getting into the street market. The dramatically changed economics has made overdose almost inevitable with heroin or cocaine laced with these synthetic opioids which are more potent but much cheaper and easier to produce. Traditional focus on source control in fighting this epidemic is simply no longer effective or efficient. Efforts have to be focused on drug safety education, treatment and prevention of patient overdose and relapse. Among these tasks, overdose prevention and treatment become the most urgent need.

As the inventors have understood opioid addiction as driven by a learned association of withdrawal relief, successful addiction treatment plans have to be holistic to include medical, psychological, behavioral and social aspects. Pharmacotherapy is essential in several treatment stages—detoxification, stabilization and prevention of relapse. It stabilizes the patients and maintains them in drug abstinence state so that psychotherapy and behavior modification can proceed.

The currently available dose forms with buprenorphine, naloxone and naltrexone in the United States are shown below in Table 1.

addiction. Currently available dose forms for buprenorphine, naloxone and naltrexone can be found in Table 1. In maintenance treatment, the dose form matters as much as the medication itself as patient compliance is usually the biggest challenge. Partly in response to this challenge, FDA recently approved two injectable or implantable device/drugs specifically for treatment of opioid dependence—Vivitrol (extended release naltrexone microsphere suspension) in 2010, and Probuphine (ethyl vinyl acetate buprenorphine implant) in 2016. In Australia, a formulation of sustained release naltrexone, suitable for subcutaneous depot administration, has been used under Commonwealth Therapeutic Goods Administration Compassionate Guidelines for the treatment of dependent opioid users since August 2000.

SUMMARY

To overcome these challenges in the fabrication process of implantable drug delivery devices and to provide more design flexibility, the inventors propose to build the whole implantable drug delivery system from biocompatible materials using more benign and flexible fabrication processes than the conventional optical lithography. In the current invention, we disclose fabrication methods utilizing either a "maskless" direct fabrication process or a "maskless" lithography process.

In this description, "Mask", as commonly understood in the semiconductor industry, is a layer of solid material which contains a predefined pattern in terms of transmission of specific light (photons), specific ion beam, an electron beam or even x-ray. In a conventional lithography setup, by flood exposure of a light-sensitive material ("resist") through the mask with or without image reduction, the predefined pattern in the mask will be transferred into the resist layer as the resist goes through certain reactions and change its properties where it is exposed to the incoming photons, ions or electrons.

"Pattern transfer layer" is a layer of material or layers of materials that facilitate transfer a predefined pattern of the mask into the final target material. In the above-mentioned example, "resist" is a common pattern transfer layer. In a broader definition of "mask", the pattern transfer layer can be treated as a new "mask" to pattern the underlying layers of materials after itself is patterned in a preceding process

TABLE 1

| Trade Name | Medication | Dosage forms | Company |
|---|---|---|---|
| Subutex | Buprenorphine | 2 and 8 mg sublingual tablets | Reckitt Benckiser |
| Suboxone | Buprenorphine/naloxone | 2-11.4 mg sublingual tablets | Reckitt Benckiser |
| Zubsolv and Generic | | Buprenorphine/naloxone 4:1 Thin film (8 mg/2 mg) | Orexo-AB |
| Bunavail | Buprenorphine/naloxone | Buccal film buprenorphine/naloxone: 2.1 mg/0.3 mg, 4.2 mg/0.7 mg and 6.3 mg/1 mg | Bio-Delivery Sciences |
| Probuphine | Buprenorphine | ethyl vinyl acetate (EVA) implant (26 mm in length and 2.5 mm in diameter) 74.2 mg of buprenorphine (up to 6 months) | Titan Pharmaceuticals |
| NARCAN | Naloxone HCl | 4 mg nasal spray | ADAPT Pharma, Inc |
| Evzio | Naloxone HCl | 0.4 mg autoinjector | Kaleo, Inc |
| Naloxone | Naloxone HCl | 0.4 mg USP | Hospira, Inc. |
| Vivitrol | Naltrexone | 380 mg in a microsphere formulation monthly Intramuscular (IM) administration | Alkermes, Inc. |

Both opioid agonists, such as methadone and buprenorphine (BUP), and opioid antagonists, such as naloxone (NLX) and naltrexone (NTX), have been approved by the Federal Drug Administration (FDA) for treatment of drug step. For clarity of description, we only use the narrow definition of "mask" as set forth in the previous paragraph. In most cases, the final target material to be patterned is not necessarily sensitive to any of the light, or particle beams that are possibly used in the lithography process. The top pattern transfer layer would typically contain molecules that are sensitive to the incoming photons, ions or electrons during the exposure. Through exposure and development processes, the predefined pattern of a mask will be transferred into the top pattern transfer layer. In some complicated cases, for the purpose of material selectivity or dimensional control, multiple patter transfer layers may be used. The pattern is transferred layer by layer from top to bottom until the final target material is patterned in a pattern transfer process, such as etch.

Maskless fabrication processes have their well known advantages and disadvantages. They are inherently more flexible with pattern design as the pattern to write can be adjusted on the fly according to the surface and location, and don't require a rigid substrate as no direct contact with the substrate is needed. These advantages are very important when patterning compliant, irregular substrates such as the biocompatible polymers. As these substrates will need to be assembled first before patterning for improved throughput and productivity, the accuracy and spatial resolution in positioning compliant, irregular substrates during an assembly process are 10s of micrometers at best, any mask with fixed patterns will have huge pattern registration issues. Surface topography of the assembled compliant irregular substrates can pose another challenge to the limited depth of focus of conventional lithography. In optical lithography, that means variation in exposure dose at the layer to be patterned, resulting in pattern distortion and poor dimensional control. In contrast, in maskless processes, the field of processing and the focus can be easily adjusted according to local misalignment and surface topography.

The disadvantages of maskless fabrication processes are associated with the low throughput and higher cost as sequential processes. These disadvantages can be overcome by limiting the use of the sequential process to a very thin pattern transfer layer and relying on subsequent parallel patter transfer processes to finally open apertures in the target biocompatible materials.

Direct writing is another fabrication process that doesn't utilize a mask. Laser drilling is one of the direct writing techniques. Direct writing differs from maskless lithography in that direct writing patterns the target material in one single process step. It has all the advantages and disadvantages as in the case of laser drilling mentioned above. However, in the case of direct writing with focused ion beams (FIB), benefits in process simplicity and biocompatibility overweigh the throughput concern of the sequential process. Typical focused ion beam uses energetic Gallium ions to mill through various materials with down to nanometer precision. A biocompatible metal overcoating, such as Titanium, is usually applied prior to ion milling, but this overcoating is more to mitigate the surface charging instead of to facilitate pattern transfer. Other approaches can also be used to neutralize the surface changes, such as electron flood gun, or insertion of an electrically conductive core. The beauty of FIB is that it can mill through a stack of heterogeneous materials without any selectivity. A single FIB process can effectively open an aperture in the biocompatible enclosure without the need of other processes. Certainly, when embedded Gallium ions on the sidewalls become a concern for biocompatibility, we can follow the aperture opening process with a mild oxidative "ashing" process, using low power oxygen plasma or CO or CO2 plasma, etc. to remove the Gallium residues and further smoothen the sidewall profile. This ashing process can also be implemented with reductive plasmas, such as hydrogen-based plasma, such as Hydrogen/Helium or Hydrogen/Argon plasma etc. The purpose of such an ashing process is to generate oxygen or hydrogen radicals and ions in the plasma and the reaction of these reactive species with the biocompatible polymer molecules will result in volatile byproducts, leading to removal of a surface layer.

One embodiment of the maskless fabrication processes using focused ion beams is focused oxygen ion beam direct writing.

Another embodiment of the maskless fabrication processes using focused ion beams is focused carbon cluster ion beam direct writing. One example of such carbon cluster ions is C60.

Both oxygen and carbon-based ion beams can be more benign than other ion beams. As a result, fewer contaminants will remain in the biocompatible enclosure. This can help maintain the biocompatibility of the whole device and simplify the fabrication process, basically by potentially eliminating the ashing process step mentioned above.

More process details of the maskless fabrication processes will be presented in the embodiments below.

Overall, the implantable drug delivery devices can be fabricated using the following steps in embodiments of the invention—

1. Selection of biocompatible enclosures with properly designed shape and dimensions;
2. Cleaning and positioning these enclosures on a rigid substrate with the help of a positioning layer, such as adhesive layer or a planarizing over molding layer;
3. Patterning of apertures of desired dimensions, shapes, and sidewall profiles into the wall of the enclosures;
4. Proper cleaning and sterilization of the enclosures;
5. Loading of the active pharmaceutical ingredients;
6. Sealing of the loading ports and any remaining open ends of the enclosure.

More innovative patterning processes for step 3 have been discussed in more details above. Besides the maskless lithography and maskless direct writing processes, more conventional lithography processes, such as those using photomasks and shadow masks, can be used, only at the risk of high defectivity and inadequate control over the dimensions, shape and sidewall profile. To transfer the pattern into the wall of the enclosures, a parallel pattern transfer process, such as reactive oxygen ion etch, is needed after the lithography processes, but may not be needed after the direct writing processes.

The step of positioning the biocompatible enclosures is critical for productivity. Accurate positioning of these enclosures and preventing them from further position shifts during the subsequent process steps can significantly reduce the degree of misalignment that the maskless patterning process has to accommodate. The smaller the misalignment, the easier the adjustments during the maskless patterning process, the faster the whole process.

One embodiment of the positioning step is to use a thermal release tape. This tape can be adhesive at room temperature, but loses its adhesiveness at elevated temperature. One envisioned process would comprise applying the thermal release tape on a silicon or glass support plate and then assembling the enclosures into an array on the tacky surface of the tape. After finishing the patterning process, the finished enclosures can be removed easily from the tape by backside heating to reduce the tackiness of the tape.

One variation of the above mentioned embodiment is the use of a light releasable adhesive tape. This is especially useful when glass support plate is used. The removal process ("detape") can be done by illuminating the tape from the backside with a light source, such as a UV lamp.

Another embodiment of the positioning step is to use an adhesive layer which is put down with sufficiently low viscosity and proper thickness prior to placement of the enclosures. The low viscosity and thickness of the adhesive layer can help position the enclosures and prevent them from moving after placement of the enclosures with optimal downward force with or without an additional curing step, i.e. a step to induce more crosslinking in the adhesive layer in order to lock the enclosures into position. In some cases, the surface tension can even help align the enclosures into a more regular array or orientation, which helps the subsequent lithography process.

One variation of the above mentioned embodiment is to a positioning layer containing a locking mechanism. In this case, the positioning layer doesn't have to be adhesive. The locking mechanism can be of the reversed shape of a feature on the enclosure. The depth of the locking mechanism should be sufficient to hold the enclosures in place during the subsequent process steps. For example, the positioning layer can be a Poly(methyl methacrylate) (PMMA) layer. It is patterned first to create an array of matching features that will be further used to lock the placed enclosures. In the case of polyimide tubes, an array of trenches matching the dimensions of the polyimide tubes are to be patterned into the PMMA layer. And then the polyimide tubes will be loaded into the trenches to prevent them from moving during the subsequent process steps.

Further, the enclosures assembled on the rigid support can be coated with a planarization layer, such as PMMA or resist. This planarization layer serves two purposes—one is to reduce the surface topography as the name of planarization implies, and the other is to use the curing process of the PMMA to position the enclosures and hold them in position during the subsequent process steps. In the case of resist, the planarization layer can also serve as the pattern transfer layer to be used in the patterning process.

The above embodiments to position, fix and planarize the array of enclosures can be combined to improve the efficiency of assembly and surface planarization.

In all these embodiments, whenever materials that are not biocompatible, such as adhesive and tapes, are used in contact with the enclosures, a subsequent cleaning and sterilization process may be required to remove any remaining residues of the materials that are not biocompatible.

While not limited to the aspects described above, embodiments disclosed herein address these and other issues in current processes.

Exemplary embodiments of the present disclosure include devices, systems and methods for long term controlled delivery of active agents, including for example, fabrication methods for devices configured to provide such delivery.

As noted above, existing fabrication processes for such devices include several limitations. Embodiments of the fabrication processes disclosed herein address numerous shortcomings in existing techniques.

For example, exemplary embodiments utilize parallel processing (including for example, maskless lithography or etching) to form apertures in non-planar enclosures. This provides more consistent control over the size and spacing of the apertures as compared to processes that individually create each aperture. The use of an adhesive layer between the non-planar enclosures and the planar substrate allows the non-planar enclosures to be assembled into an array, and the use of a planarization layer provides for more consistent patter transfer. In certain embodiments, resolution on the order of 10 nanometers can be achieved, as opposed to tens of micron level in conventional techniques such as laser drilling.

Embodiments of the present invention also relate to an implantable or injectable therapeutic agent delivery device that is capable of delivering a diagnostic, therapeutic, and/or prophylactic agent, and in its variations is capable of delivering multiple diagnostic, therapeutic, and/or prophylactic agents in a controlled manner, in order to achieve a desired pharmacokinetic profile. Optionally, the delivery device can regulate the release rates proactively or reactively in response to monitored levels of bodily fluid analytes by incorporation of microelectronic components. Additionally, the release of the agent from the device is unidirectional and at a controlled desirable rate. The active agent may include, but is not limited to, drugs, proteins, peptides, biomarkers, bioanalytes, and/or genetic material.

Embodiments of the present invention can be adapted for implantation, injection, ingestion or placement in or on a living organism, attachment to the medical device, placement in soil, water or food, attachment to an aquarium feeder, and combinations and modifications thereof.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

Certain embodiments include a method of making a device for delivery of one or more active agents with short or long zero-order release kinetics, where the method comprises: providing a substrate, and a plurality of non-planar enclosures, wherein the substrate comprises a first side and a second side; coupling the plurality of non-planar enclosures to the first side of the planar substrate; fabricating a plurality of apertures in the plurality of non-planar enclosures, wherein the plurality of apertures are fabricated via a maskless fabrication process; and loading the one or more active agents in the plurality of non-planar enclosures.

Particular embodiments further comprise separating the plurality of non-planar enclosures from the planar substrate. In some embodiments, each of the plurality of non-planar enclosures comprises an interior cavity and at least one open end, and loading the one or more active agents in the plurality of non-planar enclosures comprises: placing the one or more active agents in the interior cavity via the open end; and sealing the open end of the interior cavity. In specific embodiments, the plurality of non-planar enclosures are positioned on the first side of the substrate using an adhesive layer, a molding layer or a combination of both.

In specific embodiments, the maskless fabrication process utilizes a computer programmed and controlled focused ion beam or multiple focused ion beams to fabricate the plurality of apertures in the plurality of non-planar enclosures without using a pattern definition and transfer process (e.g. in a conventional patterning process). In certain embodiments, the ion beam is made of biocompatible and reactive ions, such as oxygen or hydrogen ions. In particular embodiments, the maskless fabrication process utilizes a pattern definition and transfer process comprising: depositing a pattern definition layer on the plurality of non-planar enclosures; forming patterns of the apertures in the pattern definition layer using a maskless lithography process; and transferring the patterns into the plurality of non-planar enclosures using an etch process.

In some embodiments, the maskless lithography process utilizes a computer programmed and controlled single electron beam or multiple electron beams. In specific embodiments, the maskless lithography process utilizes laser direct imaging, where the pattern to be imaged is programmed on a computer and projected with controlled light beam or beams. In certain embodiments, the adhesive layer comprises a tape with an adhesive first side and an adhesive second side. In particular embodiments, the molding layer is a pattern definition layer in the maskless lithography process, such as e-beam resist, or photoresist. In some embodiments, the plurality of non-planar enclosures comprises a plurality of tubular enclosures. In specific embodiments, the plurality of non-planar enclosures comprises a plurality of spherical enclosures. In certain embodiments, the planar substrate is a silicon wafer. In particular embodiments, the plurality of non-planar enclosures comprises tubular polyimide structures. In some embodiments, the maskless fabrication process comprises forming apertures in a pattern transfer layer before transferring the aperture patterns into the plurality of enclosures. In specific embodiments, the pattern transfer layer is a biocompatible dielectric pattern transfer layer.

In certain embodiments, the dielectric pattern transfer layer is a spin on glass pattern transfer layer. In particular embodiments, the dielectric pattern transfer layer is an amorphous carbon pattern transfer layer. In some embodiments, the pattern transfer layer is a biocompatible metal pattern transfer layer. In specific embodiments, the metal pattern transfer layer is a titanium layer. In certain embodiments, the aperture patterns are formed with direct writing processes utilizing electron beam(s), or ion beam(s) or laser beam(s). In particular embodiments, the maskless fabrication process utilizes a release layer.

Certain embodiments include a method of making a device for delivery of one or more active agents with zero-order release kinetics, where the method comprises: providing a planar substrate, an adhesive layer, and a plurality of non-planar enclosures, wherein the planar substrate comprises a first side and a second side; coupling the plurality of non-planar enclosures to the first side of the planar substrate with the adhesive layer; forming a pattern on the plurality of non-planar enclosures with a mask; fabricating a plurality of apertures in the plurality of non-planar enclosures with the pattern formed by the mask; and loading the one or more active agents in the plurality of non-planar enclosures. In particular embodiments, the mask is a shadow mask, and in some embodiments, the mask is a photo mask. Specific embodiments further comprise separating the plurality of non-planar enclosures from the planar substrate.

In certain embodiments, each of the plurality of non-planar enclosures comprises an interior cavity and at least one open end, and loading the one or more active agents in the plurality of non-planar enclosures comprises: placing the one or more active agents in the interior cavity via the open end; and sealing the open end of the interior cavity. In particular embodiments, the adhesive layer comprises a tape with an adhesive first side and an adhesive second side. In some embodiments, the plurality of non-planar enclosures comprises a plurality of tubular enclosures. In specific embodiments, the plurality of non-planar enclosures comprises a plurality of spherical enclosures.

Certain embodiments include a device for delivery of one or more active agents capable of zero-order delivery kinetics comprising: a homogenous, impermeable, biocompatible housing containing a hollow core; one or more passageways made of micrometer scale out of the same homogenous and biocompatible material; one or more loading ports to load the active agents into the housing; and sealing caps or fillings applied to the loading ports and/or the passageways.

Particular embodiments further comprise multiple homogenous, impermeable, biocompatible housings each of which comprises one or more passageways to enable individual release rates of therapeutic agents from the housings. In some embodiments, the homogenous, impermeable, biocompatible housing comprises multiple partitioned compartments (hollow cores) each of which comprises one or more passageways to enable individual release rates of therapeutic agents from the compartments. In specific embodiments, the hollow core is loaded with a composition or formulation of one or more therapeutic agents which are to be released at their individual release rates. In certain embodiments, the sidewall surface of the passageways has a roughness smaller than 5% of the smallest inner diameter of the passageways. In particular embodiments, the inner diameter of the passageways is larger than the size of common proteins and/or cells that the device may encounter in an anatomic implant site and smaller than the maximum size limit which may significantly affect the sink condition required for zero-order delivery kinetics.

In some embodiments, the inner diameter of the passageways is in the range of 0.1 µm-500 µm, 1-100 µm, 10-50 µm or 20-30 µm. In specific embodiments, the device is coated with a biodegradable coating that prevents release of the one or more active agents until the coating is dissolved in bodily fluids, which then causes release of the one or more active agents at a substantially constant rate.

In certain embodiments, the device is coated with a coating which comprises a remotely activatable switching mechanism that when not activated, prevents release of the one or more active agents, and causes release of the one or more active agents at a substantially constant rate when the mechanism is activated. In particular embodiments, the housing comprises an area which can be used to recharge the device in-situ with therapeutic agents.

Certain embodiments include an implantable or injectable drug delivery system capable for controlled release over long periods of time intended for drug addiction treatments, comprising a biocompatible polyimide housing impermeable to the bodily fluids, a hollow core filled with supply of certain opioid agonists and/or opioid antagonists or its compounds, and one or more passageway(s) or channel(s) built into the otherwise impermeable wall of the housing. In specific embodiments, the periods of time include one hour to one day, one day to one week, one week to one month, one month to one year, or one year to ten years. In particular embodiments, the opioid agonist includes buprenorphine and methadone. In some embodiments, the opioid antagonist includes naloxone and naltrexone.

In some embodiments, the system comprises a composition or formulation of therapeutic agents to treat drug addiction which includes a mix of at least an opioid agonist and an opioid antagonist. In specific embodiments, the system comprises at least two biocompatible polyimide housings impermeable to the bodily fluids, with the first housing comprising an opioid agonist and the second housing comprising an opioid antagonist. In certain embodiments, the system comprises one biocompatible polyimide housing impermeable to the bodily fluids which further comprises at least two partitioned hollow cores with the first hollow core comprising an opioid agonist and the second hollow core comprising an opioid antagonist. In particular embodiments, the housing comprises an area which can be used to recharge the system in-situ with a supply of the therapeutic agents. In some embodiments, the inner diameter of the passageways is in the range of 0.1 μm-500 μm, 1-100 μm, 10-50 μm or 20-30 μm.

Certain embodiments include an implantable or injectable drug delivery system capable for controlled release over long periods of time for mTOR inhibitors, such as rapamycin and its analogs, to treat aging-related morbidities, comprising a biocompatible polyimide housing impermeable to the bodily fluids, a hollow core filled with supply of solid rapamycin and other mTOR inhibitors, and one or more passageway(s) or channel(s) built into the otherwise impermeable wall of the housing. In specific embodiments, the periods of time include one hour to one day, one day to one week, one week to one month, one month to one year, or one year to ten years. In particular embodiments, the inner diameter of the passageways is in the range of 0.1 μm-500 μm, 1-100 μm, 5-50 μm or 10-20 μm. In some embodiments, the system comprises a composition or formulation containing rapamycin or its variant mTOR inhibitors. In specific embodiments, the system comprises a composition or formulation of therapeutic agents which includes a mix of at least a rapamycin or rapalog and another drug for combination therapy.

In certain embodiments, the system comprises at least two biocompatible polyimide housings impermeable to the bodily fluids, with the first housing comprising a rapamycin or a rapalog and the second housing comprising another drug needed for combination therapy. In particular embodiments, the system comprises one biocompatible polyimide housing impermeable to the bodily fluids which further comprises at least two partitioned hollow cores with the first hollow core comprising a rapamycin or a rapalog and the second hollow core comprising another drug needed for combination therapy.

In some embodiments, the system is coated with a biodegradable coating that prevents release of the one or more active agents until the coating is dissolved in bodily fluids, which then causes release of the one or more active agents at a substantially constant rate. In specific embodiments, the system is coated with a coating which comprises a remotely activatable switching mechanism that when not activated, prevents release of the one or more active agents, and causes release of the one or more active agents at a substantially constant rate when the mechanism is activated.

Certain embodiments include an implantable or injectable drug delivery system capable for controlled release over long periods of time for therapeutic agents to treat pancreatic cancers, comprising a biocompatible polyimide housing impermeable to the bodily fluids, a hollow core filled with supply of proper therapeutic agents, and one or more passageway(s) or channel(s) built into the otherwise impermeable wall of the housing. In specific embodiments, the periods of time include one hour to one day, one day to one week, one week to one month, one month to one year, or one year to ten years.

In certain embodiments, the inner diameter of the passageways is in the range of 0.1 μm-500 μm, 1-100 μm, 5-50 μm or 10-20 μm. In particular embodiments, the outer diameter of the housing is in the range of 50 μm-2000 μm, 500-1000 μm. In some embodiments, the system comprises a composition or formulation containing therapeutic agents for chemotherapy of pancreatic cancers, including ABRAXANE® (albumin-bound paclitaxel), GEMZAR® (gemcitabine), 5-FU (fluorouracil) and ONIVYDE® (irinotecan liposome injection). In specific embodiments, the system is coated with a biodegradable coating that prevents release of the one or more active agents until the coating is dissolved in bodily fluids, which then causes release of the one or more active agents at a substantially constant rate. In certain embodiments, the system is coated with a coating which comprises a remotely activatable switching mechanism that when not activated, prevents release of the one or more active agents, and causes release of the one or more active agents at a substantially constant rate when the mechanism is activated.

Certain embodiments include an implantable or injectable drug delivery system capable for controlled release over long periods of time for therapeutic agents to be implanted into the brain for treatment of neurodegenerative diseases, comprising a biocompatible polyimide housing impermeable to the bodily fluids, a hollow core filled with supply of the therapeutic agents, and one or more passageway(s) or channel(s) built into the otherwise impermeable wall of the housing.

In specific embodiments, the periods of time include one hour to one day, one day to one week, one week to one month, one month to one year, or one year to ten years. In particular embodiments, the inner diameter of the passageways is in the range of 0.1 μm-500 μm, 1-100 μm, or 1-20 μm. In some embodiments, the outer diameter of the housing is in the range of 20 μm-2000 μm, or 50-1000 μm. In specific embodiments, the system is coated with a biodegradable coating that prevents release of the one or more active agents until the coating is dissolved in bodily fluids, which then causes release of the one or more active agents at a substantially constant rate. In certain embodiments, the system is coated with a coating which comprises a remotely activatable switching mechanism that when not activated, prevents release of the one or more active agents, and causes release of the one or more active agents at a substantially constant rate when the mechanism is activated.

To facilitate the understanding of this invention, a number of terms are defined below. Terms defined herein have meanings as commonly understood by a person of ordinary skill in the areas relevant to the present invention. The terminology herein is used to describe specific embodiments of the invention, but their usage does not delimit the invention, except as outlined in the claims.

Before any embodiments of the invention are described in detail, it is to be understood that the invention is not limited in its application to the details of construction and the arrangement of components set forth in the following description. The invention is capable of other embodiments and of being practiced or of being carried out in various ways. Also it is to be understood that the phraseology and terminology used herein is for the purpose of description and should not be regarded as limiting. The use of "including," "comprising," or "having" and variations thereof herein is meant to encompass the items listed thereafter and equivalents thereof, as well as additional items.

In the present disclosure, the term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." Terms such as "a", "an" and "the" are not intended to refer to only a singular entity, but include the general class of which a specific example may be used for illustration. The terms "approximately," "about" or "substantially" mean, in general, the stated value plus or minus 10%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed. In addition, a method that recites multiple steps does not require the steps be performed in the order recited.

The term "therapeutic agent delivery device" as used herein, refers to any device that comprises a housing made of an impermeable matrix material and a hollow core filled with therapeutic agent(s) or a composition and/or formulation of therapeutic agent(s) and other assisting agent(s).

The term "housing" as used herein, refers to any impermeable matrix material, of any shape or size.

The term "hollow core" as used herein, refers to any open space encompassed by a housing, configured to contain a supply of therapeutic agent composition and/or formulation.

The term "passageway" or "channel" as used herein, refers to any means by which a drug molecule can transport from the supply in the hollow core, through and out of the housing. Such means may include but are not limited to, an aperture, orifice, bore, channel outlet, or hole. The number and size of the "passageway" may be selected to tailor the rate and extent of release of the agents. For example, the diameter of a passageway may range from several nanometers to several centimeters. Preferably, the diameter of a passageway ranges between approximately 1 nanometers-1 centimeter. More preferably, the diameter of a passageway ranges between approximately 100 nanometers-750 microns. Even more preferably, the diameter of a passageway ranges between approximately 5 microns (micrometers)-500 microns (micrometers). Preferably, the diameter of a passageway ranges between approximately 10 microns-100 microns.

The term "outlet port" as used herein, refers to any open end of a hollow core.

The term "therapeutic agent" as used herein, refers to any pharmacologically active substance capable of being administered which achieves a desired effect. Such agents can be synthetic or naturally occurring, cells, non-peptide, proteins or peptides, oligonucleotides or nucleotides, polysaccharides or sugars.

The term "administered" or "administering" a therapeutic agent, as used herein, refers to any method of providing an agent to a patient such that the agent has its intended effect on the patient. For example, administering may include but not limited to, local tissue administration (i.e., for example, via a drug delivery device), oral ingestion, transdermal patch, topical, inhalation, suppository etc.

The term "therapeutic agent supply" as used herein, refers to any drug depot or reservoir that can support a certain drug dosage profile over an extended period of time, and in a form including, but not limited to, a solid composition, a hydrogel, a colloid, a suspension, solution, or powder that is placed within a hollow core.

The term "drug" as used herein, refers to any therapeutically or prophylactically active agent, wherein the agent obtains a desired diagnostic, physiological, or pharmacological effect. For example, a drug may include, but is not limited to, any compound, composition of matter, or mixture thereof that may be natural or synthetic, organic or inorganic molecule or mixture thereof which may be used as a therapeutic, prophylactic, or diagnostic agent. Some examples include but are not limited to chemotherapeutic agents such as monoclonal antibodies, 5-fluorouracil, gemcitabine, paclitaxel, sirolimus, adriamycin, and related compounds; antifungal agents such as fluconazole and related compounds; anti-viral agents such as trisodium phosphomonoformate, trifluorothymidine, acyclovir and related compounds; cell transport/mobility impending agents such as colchicine, vincristine, cytochalasin B and related compounds; antiglaucoma drugs such as beta blockers: timolol, betaxolol, atenolol, an related compounds; peptides and proteins such as insulin, growth hormones, insulin related growth factors, enzymes, and other compounds; steroids such as dexamethasone, prednisone, prednisolone, ethinyl estradiol, and similar compounds; antihypertensives, anti-convulsants, blood glucose lowering agents, diuretics, painkillers, opioid agonists (e.g., methadone and buprenorphine), opioid antagonists, (e.g., naloxone and naltrexone), blood thinning agents, anesthetics, antibiotics, antihistaminics, immunosuppressants (e.g., mTOR inhibitors, rapamycin and its variants), anti-inflammatory agents, anti-oxidants, in vivo diagnostic agents (e.g., contrast agents), sugars, vitamins, toxin antidotes, and molecules developed by gene therapy.

The term "bodily fluid" as used herein refers to any liquid-like or semi-solid composition derived from an organism including but not limited to blood, serum, urine, gastric, and digestive juices, tears, saliva, stool, semen, and interstitial fluids derived from tumorous tissues.

The term "analyte" as used herein, refers to any compound within a body fluid including, but not limited to, a small amount of organic molecule, mineral, inorganic ions, protein, or hormone.

The term "biopharmaceutical classification system" or "BCS" as used herein, refers to a scientific classification framework for drug substances based on their aqueous solubility and intestinal permeability (US Dept. Health & Human Services, Food and Drug Administration Center for Drug Evaluation and Research (CDER) August 2000).

The term "permeability" as used herein, refers to any material that permits liquids or gases to pass through. The term "impermeable" as used herein, refers to any material that does not permit liquids or gases to pass through.

The term "solubility" as used herein, refers to the amount of a substance that will dissolve in a given amount of another substance. Typically solubility is expressed as the number of parts by weight dissolved by 100 parts of solvent at a specified temperature and pressure or as percentage by weight or by volume.

The term "controlled release" as used herein, refers to a predictable transport of a therapeutic agent through and out of the housing that may be described by mathematical relationships. For example, a controlled release may follow zero order kinetics.

The term "zero-order kinetics" as used herein, refers to a constant controlled release of a therapeutic agent wherein the release rate is a substantially constant rate that does not significantly change during the consumption of a therapeutic drug supply (i.e., the release rate maintains linearity throughout the consumption of the drug supply).

The term "substantially constant rate" as used herein, refers to a zero order kinetic release of a therapeutic agent wherein a regression coefficient is at least 0.90 (i.e., for example, R2).

The term "long-term administration" as used herein, refers to any therapeutic agent that is given to a patient or subject at greater than a single dose equivalent. For example, such administration may comprise multiple doses on a single day or a single dose over several days. Alternatively, such administration may comprise a continuous substantially constant rate over periods of hours, days, weeks or years.

The terms "extended period(s) of time" or "long period(s) of time" include time periods of hours, days, weeks or years.

The term "geometrical shape" as used herein, refers to any custom designed composition that is formulated for implantation into a specific anatomical site of a biological organism. For example, such compositions may include but are not limited to, a cuboid, a cube, a sphere, a cone, an oval, or a cylinder. In particular, a cube is shaped having six sides of equal area whereas a cuboid in the broadest sense includes, but is not limited to, polygonal, rhombus, trapezoid, rectangular, and square cross-sectional shapes with substantially squared or rounded corners and with perpendicular or angled sides.

The term "loading" or "loaded" as used herein, refers to the placement of a therapeutic agent supply within the hollow core of a drug delivery device. On the other hand, a device may be provided that is "preloaded" with a therapeutic agent supply, The term "body lumen" as used herein, refers to any cavity of a tubular body organ (i.e., for example, the interior of a blood vessel).

The term "biocompatible" as used herein, refers to any material does not elicit a substantial detrimental response in the host. There is always concern, when a foreign object is introduced into a living body, that the object will induce an immune reaction, such as an inflammatory response that will have negative effects on the host. In the context of this invention, biocompatibility is evaluated according to the application for which it was designed: for example; an implanted medical device (i.e., for example, an impermeable therapeutic agent delivery device) is regarded as biocompatible with the internal tissues of the body. Preferably, biocompatible materials include, but are not limited to, biodegradable and biostable materials.

The term "biodegradable" as used herein, refers to any material that can be acted upon biochemically by living cells or organisms, or processes thereof, including water, and broken down into lower molecular weight products such that the molecular structure has been altered.

The term "bioresabsorbable" as used herein, refers to any material that is assimilated into or across bodily tissues. The bioresorption process may utilize both biodegradation and/or bioerosin.

The term "non-biodegradable" as used herein, refers to any material that cannot be acted upon biochemically by living cells or organisms, or processes thereof, including water.

The term "non-bioreabsorbable" as used herein, refers to any material that cannot be assimilated into or across bodily tissues.

The term "medical device" as used herein, refers broadly to any apparatus used in relation to a medical procedure and/or therapy. Specifically, any apparatus that contacts a patient during and/or after a medical procedure or therapy is contemplated herein as a medical device. Similarly, any apparatus that administers a drug composition and/or formulation to a patient during or after a medical procedure and/or therapy is contemplated herein as a medical device. Such devices are usually implanted and may include, but are not limited to, urinary and intravascular catheters, dialysis shunts, wound drain tubes, skin sutures, vascular grafts and implantable meshes, intraocular devices, implantable drug delivery devices or systems (i.e., for example, a stent or eye buckle) and heart valves, and the like. A medical device is "coated" when a medium (i.e., for example a polymer) comprising a therapeutic agent becomes attached to the surface of the medical device. This attachment may be permanent or temporary. When temporary, the attachment may result in a controlled release of a drug.

The term "attached" as used herein, refers to any interaction between a medium (or carrier) and a drug. Attachment may be reversible or irreversible. Such attachment includes, but is not limited to, covalent bonding, ionic bonding, Van der Waals forces or friction, and the like. A drug is attached to a medium (or carrier) if it is impregnated, incorporated, coated, in suspension with, in solution with, mixed with, etc.

The term "anatomical site" as used herein refers to any internal or external, deep or superficial body cavity, lumen, tissue, or organ of a mammalian organism. Some examples of anatomical sites where the medical device can be placed includes, but is not limited to, eyes, toenails, fingernails, epidermis (i.e., for example, skin), nasal cavity, gastro intestinal tract, valves, veins, and arteries such as coronary arteries, renal arteries, aorta, cerebral arteries, including for example, a cerebral arterial wall.

The terms "reduce," "inhibit," "diminish," "suppress," "decrease," "prevent" and grammatical equivalents (including "lower," "smaller," etc.) when in reference to the expression of any symptom in an untreated patient relative to a treated patient, mean that the quantity and/or magnitude of the symptoms in the treated patient is lower than in the untreated patient by any amount that is recognized as clinically relevant by any medically trained personnel. In one embodiment, the quantity and/or magnitude of the symptoms in the treated patient is at least 10% lower than, preferably, at least 25% lower than, more preferably at least 50% lower than, still more preferably at least 75% lower than, and/or most preferably at least 90% lower than the quantity and/or magnitude of the symptoms in the untreated patient.

The term "patient", as used herein, is a human or animal and need not be hospitalized. For example, out-patients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "effective amount" as used herein, refers to a particular amount of a pharmaceutical composition comprising a therapeutic agent that achieves a clinically beneficial result (i.e., for example, a reduction of symptoms). Toxicity and therapeutic efficacy of such compositions can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index, and it can be expressed as the ratio LD50/ED50. Compounds that exhibit large therapeutic indices are preferred. The data obtained from these cell culture assays and additional animal studies can be used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The term "derived from" as used herein, refers to the source of a compound or sequence. In one respect, a compound or sequence may be derived from an organism or particular species. In another respect, a compound or sequence may be derived from a larger complex or sequence.

The term "pharmaceutically" or "pharmacologically acceptable", as used herein, refer to molecular entities and compositions that for use in humans and other mammals that have been approved by a drug and medical device regulating authority or are under clinical development and have acceptable risk to benefit ratio.

The term, "pharmaceutically acceptable carrier", as used herein, includes any and all solvents, or a dispersion medium including, but not limited to, water, ethanol, polyol (for example, glycerol, propylene glycol, and liquid polyethylene glycol, and the like), suitable mixtures thereof, and vegetable oils, coatings, isotonic and absorption delaying agents, liposome, commercially available cleansers, and the like. Supplementary bioactive ingredients also can be incorporated into such carriers.

The term "formulation" as used herein, refers to any composition comprising a therapeutic agent intended for administration to a patient and/or subject. A formulation may include, but not be limited to, a solid, a powder, a semisolid, or a gel.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

DETAILED DESCRIPTION OF ILLUSTRATIVE EMBODIMENTS

Figure 1:
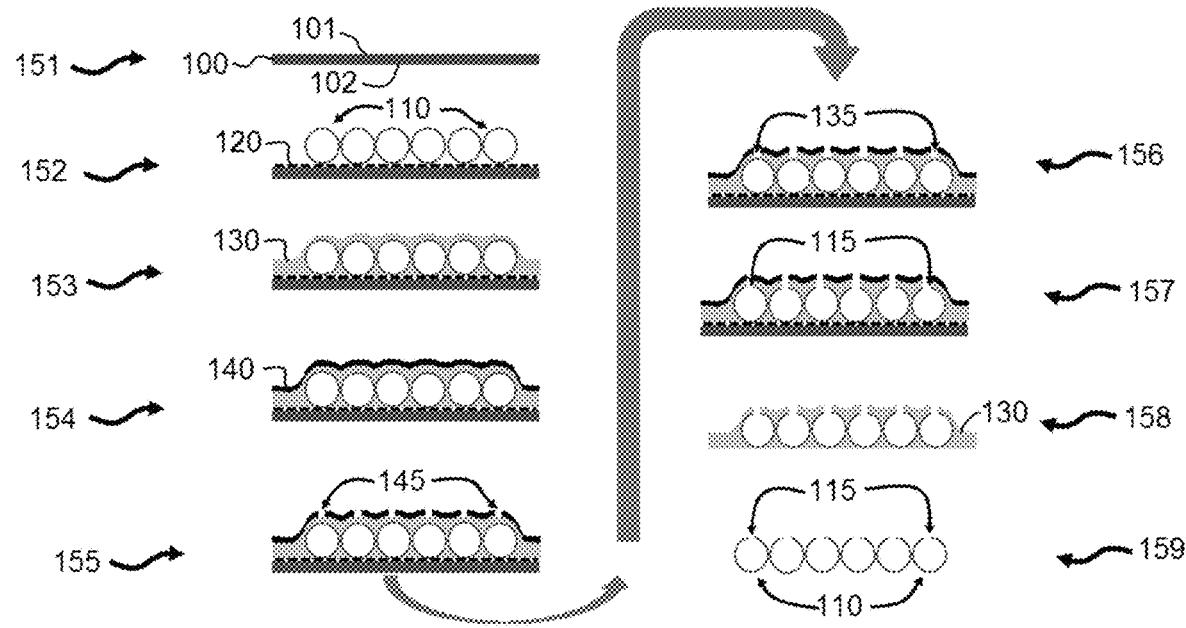
FIG. 1 illustrates an exemplary embodiment of a system and method as disclosed herein.

Referring initially to FIG. 1, a series of steps are shown in a method for making a device for delivery of one or more active agents with zero-order release kinetics. In the illustrated method, a planar substrate 100 with first side 101 and a second side 102 is initially provided as shown in step 151. In a particular embodiment, planar substrate 101 is a 2 inch by 2 inch coupon from a silicon wafer. As shown in step 152, a plurality of non-planar enclosures 110 are then coupled to first side 101 of planar substrate 100 via an adhesive layer 120. In particular embodiments, adhesive layer 120 may be configured as a double-sided polyimide tape (e.g. a tape with adhesive properties on each side) and non-planar enclosures 120 may be configured as tubular polyimide structures. It is understood that other embodiments of the present invention may comprise components with different materials or different configurations than the specific examples illustrated and described herein.

In the illustrated embodiment, a maskless fabrication process is used to fabricate a plurality of apertures 115 in non-planar enclosures 110. As used herein, the term "maskless fabrication process" is used to indicate a fabrication process that does not utilize a mask (i.e. a layer of solid material with an existing, pre-determined pattern) to form apertures in a non-planar substrate. For example, an electron beam lithography process can be combined with a dielectric spin-on glass (SOG) or amorphous carbon pattern transfer layer to fabricate apertures 115. In the embodiment shown, an SOG spin-coating 130 can be used to cover non-planar enclosures 110, adhesive layer 120 and planar substrate 100 (as shown in step 153) and cured at 300 degrees Celsius. It is also understood that the specific procedural parameters described herein are merely exemplary and that other embodiments of the present invention may comprise different parameters, including for example, different temperatures or time periods.

As shown in step 154, a resist coating 140 can then be applied over SOG coating 130 and soft baked at 180 degrees Celsius. In particular embodiments, resist coating 140 may be a positive toned e-beam resist—poly(methyl methacrylate) (PMMA) coating (such as provided by Microchem in http://www.microchem.com/pdf/PMMA_Data_Sheet.pdf). An electron beam lithography process can then be used to form apertures 145 in resist coating 140, with e-beam exposure, development with Methyl isobutyl ketone (MIBK), rinse and dry, and then post-bake at 100 degrees Celsius, as illustrated in step 155. An oxide etch can then be applied to form apertures 135 in SOG spin-coating 130 (as shown in step 156), followed by a polymer etch to form apertures 115 in non-planar enclosures 110 shown in step 157. A warm acetone bath can be applied to remove resist coating 140 and to detach planar substrate 100 as shown in step 158. Finally, a dilute hydrofluoric acid or buffered oxide etch can be used to remove SOG coating 130, followed by a clean and sterilization step to clean non-planar enclosures 110 as shown in step 159.

In certain embodiments, non-planar enclosures 110 can be used a device for delivery of one or more active agents with zero-order release kinetics. For example, one or more active agents can be located within an interior volume 119 of non-planar enclosures 110 and delivered to an outside environment (e.g. a patient in which the device has been implanted). Certain embodiments can be adapted for implantation, ingestion or placement in or on a living organism, attachment to a medical device, and placement in soil, water or food, attachment to an aquarium feeder, and combinations and modifications thereof.

Figure 2:
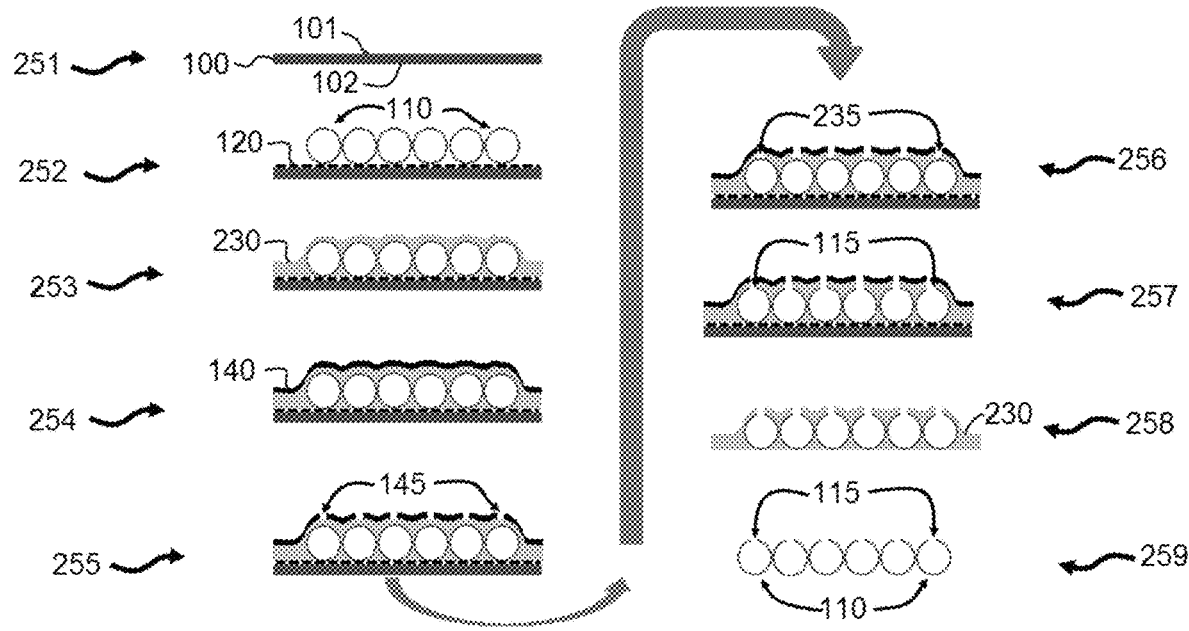
FIG. 2 illustrates an exemplary embodiment of a system and method as disclosed herein.

Referring now to FIG. 2, a series of steps are shown in a method for making a device for delivery of one or more active agents with zero-order release kinetics. This embodiment is similar to the previously-described embodiment in FIG. 1 in that a maskless fabrication process is used to fabricate a plurality of apertures 115 in non-planar enclosures 110. However, in this embodiment a biocompatible metal (e.g. titanium or aluminum/titanium) pattern transfer layer is utilized instead of a dielectric spin-on glass or amorphous carbon pattern transfer layer.

In the illustrated method, a planar substrate 100 with first side 101 and a second side 102 is initially provided as shown in step 251. In a particular embodiment, planar substrate 101 is a 2 inch by 2 inch coupon from a silicon wafer. As shown in step 252, a plurality of non-planar enclosures 110 are then coupled to first side 101 of planar substrate 100 via an adhesive layer 120.

In particular embodiments, adhesive layer 120 may be configured as a double-sided polyimide tape (e.g. a tape with adhesive properties on each side) and non-planar enclosures 120 may be configured as tubular polyimide structures. It is understood that other embodiments of the present invention may comprise components with different materials or different configurations than the specific examples illustrated and described herein.

As shown in step 253, a titanium layer 230 is then deposited (e.g. via an evaporation process). In the embodiment shown, titanium layer 230 can be used to cover non-planar enclosures 110, adhesive layer 120 and planar substrate 100. As shown in step 254, a resist coating 140 can then be applied over titanium layer 230 and prebaked to 180 degrees Celsius in the case of PMMA. In particular embodiments, resist coating 140 may be a poly(methyl methacrylate) (PMMA) coating. An electron beam lithography process can then be used to form apertures 145 in resist coating 140, as illustrated in step 255. A titanium dry etch can then be applied to form apertures 235 in titanium layer 230 (as shown in step 256), followed by a polymer etch to form apertures 115 in non-planar enclosures 110 shown in step 257. A warm acetone bath can be applied to remove resist coating 140 and to detach planar substrate 100 as shown in step 258. Finally, a titanium wet etch can be used to remove titanium layer 230, followed by a wash and dry and sterilization step to clean non-planar enclosures 110 as shown in step 259.

In still other embodiments, non-planar enclosures according to the present disclosure may be formed without a pattern transfer layer as used in the embodiments of FIGS. 1 and 2.

Figure 3:
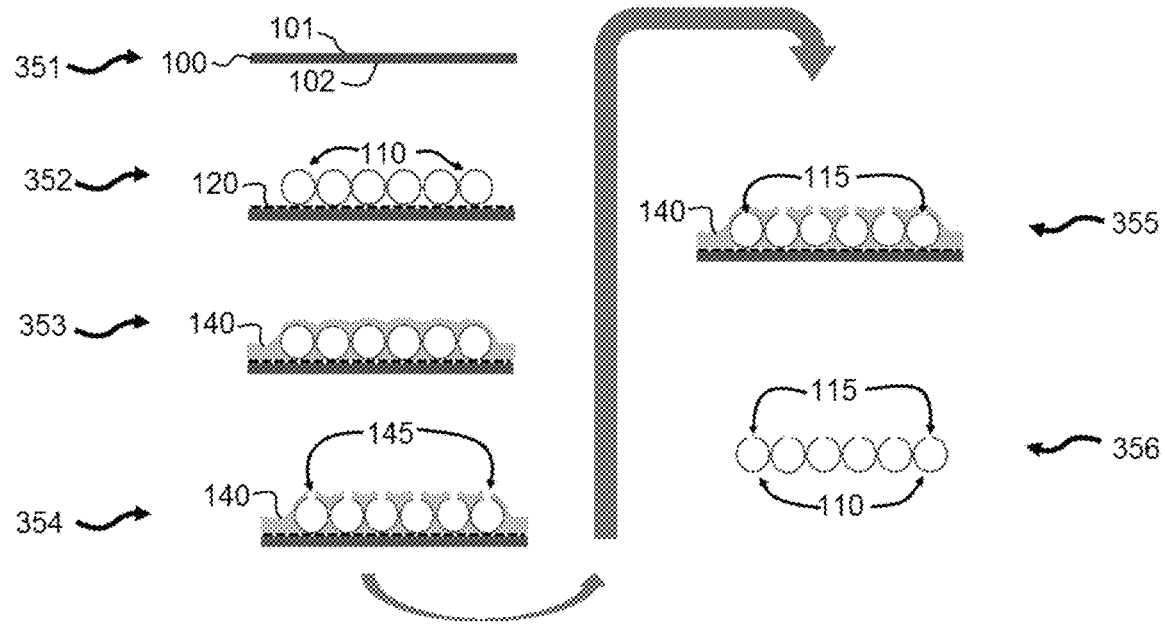
FIG. 3 illustrates an exemplary embodiment of a system and method as disclosed herein.

Referring now to FIG. 3, a series of steps are shown in another maskless fabrication process for making a device for delivery of one or more active agents with zero-order release kinetics. This embodiment is similar to the previously-described embodiment in FIGS. 1 and 2, but does not utilize the metal pattern transfer layer of FIG. 2 or the dielectric spin-on glass or amorphous carbon pattern transfer layer of FIG. 1. Instead, the embodiment of FIG. 3 does not utilize a separate pattern transfer layer.

In the illustrated method, a planar substrate 100 with first side 101 and a second side 102 is initially provided as shown in step 351. In a particular embodiment, planar substrate 101 is a 2 inch by 2 inch coupon from a silicon wafer. As shown in step 352, a plurality of non-planar enclosures 110 are then coupled to first side 101 of planar substrate 100 via an adhesive layer 120. In particular embodiments, adhesive layer 120 may be configured as a double-sided polyimide tape (e.g. a tape with adhesive properties on each side) and non-planar enclosures 120 may be configured as tubular polyimide structures. It is understood that other embodiments of the present invention may comprise components with different materials or different configurations than the specific examples illustrated and described herein.

As shown in step 353, a resist coating 140 can then be applied to cover non-planar enclosures 110, adhesive layer 120 and planar substrate 100 and prebaked. In particular embodiments, resist coating 140 may be a poly(methyl methacrylate) (PMMA) coating. An electron beam lithography process can then be used to form apertures 145 in resist coating 140, as illustrated in step 354. A polymer etch can then be used to form apertures 115 in non-planar enclosures 110 shown in step 355. A warm acetone bath can be applied to remove any residual resist coating 140 and to detach planar substrate 100 as shown in step 356.

Figure 4:
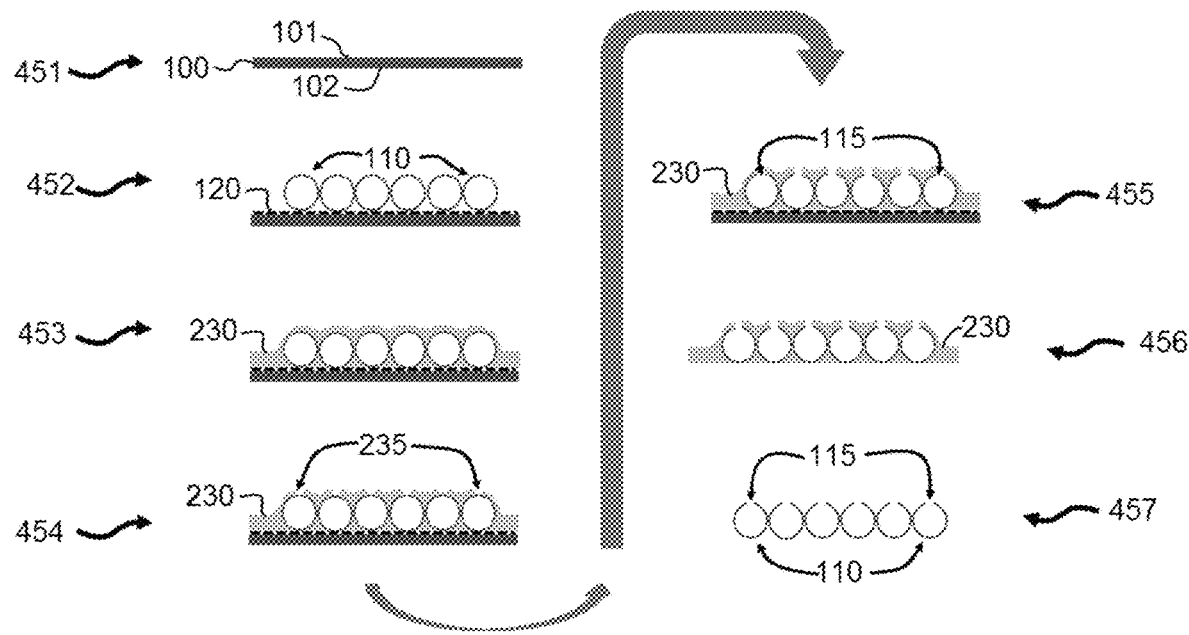
FIG. 4 illustrates an exemplary embodiment of a system and method as disclosed herein

In other embodiments, the maskless fabrication process may use a focused ion beam instead of an electron beam as used in the embodiments of FIGS. 1-3. Referring now to FIG. 4, a fabrication process similar to that shown in FIG. 2 incorporates a metal (e.g. titanium or aluminum/titanium) pattern transfer layer, but utilizes a focused ion beam instead of an electron beam.

In the illustrated method, a planar substrate 100 with first side 101 and a second side 102 is initially provided as shown in step 451. In a particular embodiment, planar substrate 101 is a 2 inch by 2 inch coupon from a silicon wafer. As shown in step 452, a plurality of non-planar enclosures 110 are then coupled to first side 101 of planar substrate 100 via an adhesive layer 120. In particular embodiments, adhesive layer 120 may be configured as a double-sided polyimide tape (e.g. a tape with adhesive properties on each side) and non-planar enclosures 120 may be configured as tubular polyimide structures. It is understood that other embodiments of the present invention may comprise components with different materials or different configurations than the specific examples illustrated and described herein.

As shown in step 453, a titanium layer 230 is then deposited (e.g. via an evaporation process). In the embodiment shown, titanium layer 230 can be used to cover non-planar enclosures 110, adhesive layer 120 and planar substrate 100. A focused ion beam lithography process can then be used to form an aperture pattern 235 in titanium layer 230, as illustrated in step 454. A polymer etch can then be applied to form apertures 115 in non-planar enclosures 110 shown in step 455. A warm acetone bath can be applied to remove resist coating 140 and to detach planar substrate 100 as shown in step 456. Finally, an optional titanium wet etch can be used to remove titanium layer 230, followed by a wash step to clean non-planar enclosures 110 as shown in step 457.

Standard focused ion beam milling equipment utilizes gallium ions which may need additional surface cleaning using oxygen plasma to remove any gallium ions that are embedded in the sidewall of apertures during the milling process. A special case would be using oxygen ions for the focused ion beam milling. The use of focused oxygen ion beam to mill through the metal layer and the polymeric wall of the drug depot can guarantee no harmful residues, thus simplifying the process and eliminating the need of additional clean steps.

Figure 5:
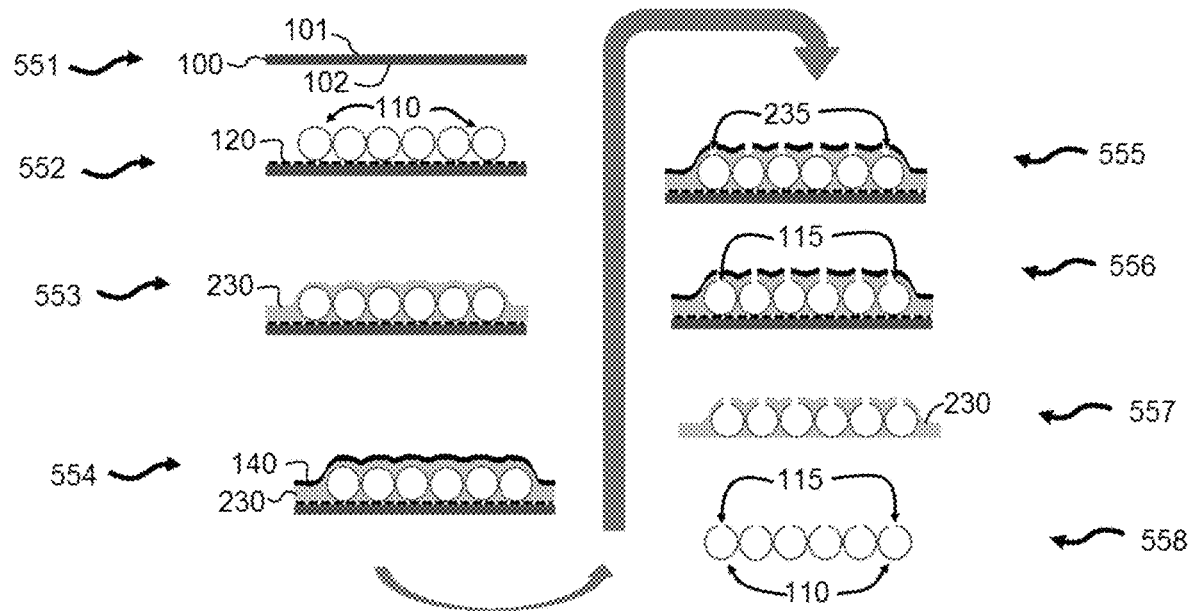
FIG. 5 illustrates an exemplary embodiment of a system and method as disclosed herein.

Referring now to FIG. 5, a maskless fabrication process is shown similar to that of FIG. 4 utilizing a focused ion beam. In the embodiment of FIG. 5, however, a release layer is also utilized. In exemplary embodiments, the release layer can be any organic or inorganic sacrificial material, (e.g., photoresist, PMMA, spin-on glass, etc.)

In the illustrated method, a planar substrate 100 with first side 101 and a second side 102 is initially provided as shown in step 551. In a particular embodiment, planar substrate 101 is a 2 inch by 2 inch coupon from a silicon wafer. As shown in step 552, a plurality of non-planar enclosures 110 are then coupled to first side 101 of planar substrate 100 via an adhesive layer 120. In particular embodiments, adhesive layer 120 may be configured as a double-sided polyimide tape (e.g. a tape with adhesive properties on each side) and non-planar enclosures 120 may be configured as tubular polyimide structures. It is understood that other embodiments of the present invention may comprise components with different materials or different configurations than the specific examples illustrated and described herein.

As shown in step 553, a release layer 530 is then deposited to cover non-planar enclosures 110, adhesive layer 120 and planar substrate 100. As shown in step 554, a titanium (or other suitable metal) layer 540 can then be applied over release layer 530. A focused ion beam lithography process can then be used to form a pattern 545 in titanium layer 540 (as shown in step 555). This is then followed by a polymer etch to form apertures 115 in non-planar enclosures 110 shown in step 556. A warm acetone batch with ultrasound can be applied to remove most of the titanium layer 540 except that adheres to the surface of the enclosure 110 and to detach planar substrate 100 as shown in step 557. Finally, a titanium wet etch can be used to remove any remaining titanium and clean non-planar enclosures 110 as shown in step 558.

Figure 6:
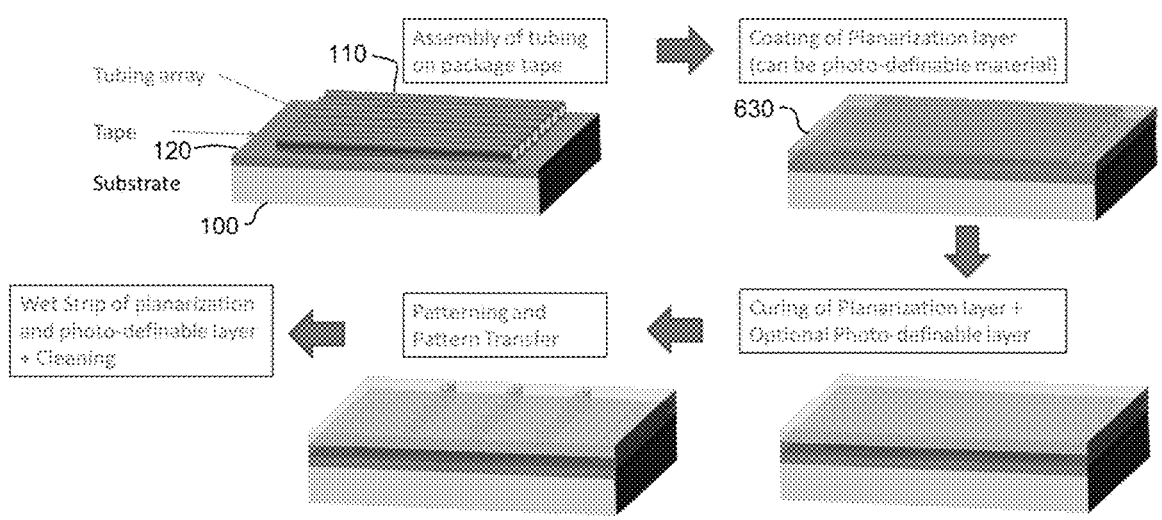
FIG. 6 illustrates an exemplary embodiment of a system and method as disclosed herein

Referring now to FIG. 6, a series of steps are shown in a fabrication process for making a device for delivery of one or more active agents with zero-order release kinetics. Unlike the previously-described maskless fabrication process, the process in FIG. 6 utilizes a photo mask. In this embodiment, non-planar enclosures 110 are coupled to substrate 100 via an adhesive layer 120. A coating of a planarization layer 630 (which may be a photo-definable material in certain embodiments) is then applied. In other embodiments, a separate planarization layer and photo-definable layer can be applied. After curing planarization layer 630 (and optional photo-definable layer, if applicable), patterning and pattern transfer using a photo mask can be used to form apertures in planarization layer 630 and non-planar enclosures 110. This can be followed by a wet strip of planarization layer 630 (and optional photo-definable layer) to separate non-planar enclosures 110 from substrate 100 and an adhesive layer 120.

Figure 7:
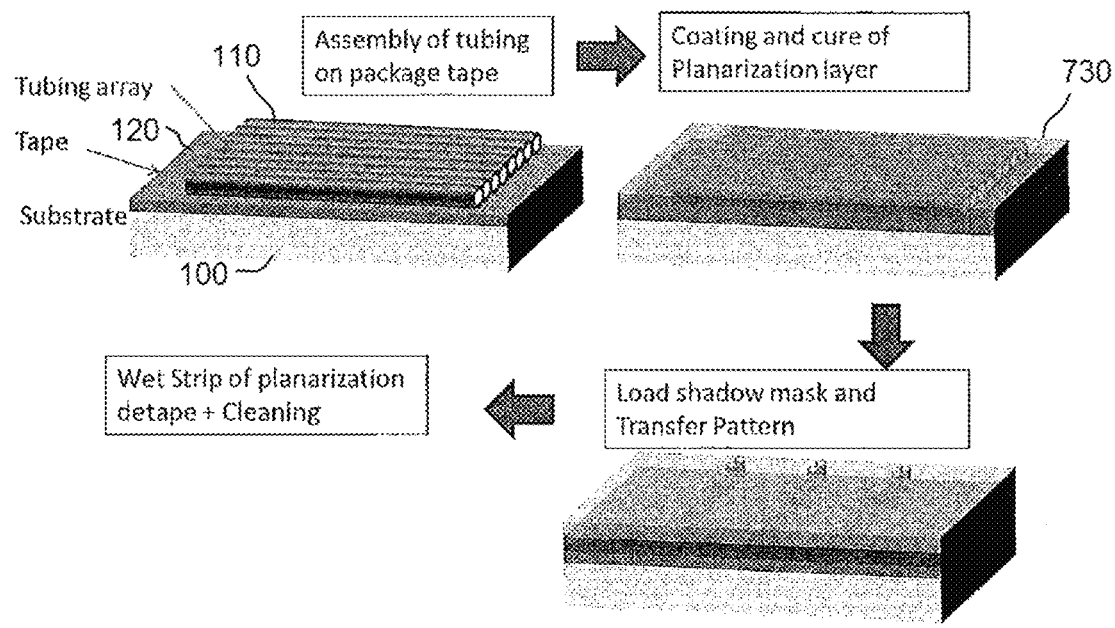
FIG. 7 illustrates an exemplary embodiment of a system and method as disclosed herein.

Referring now to FIG. 7, a fabrication process is illustrated using a shadow mask rather than the photo mask of the previously-described embodiment. In this embodiment, non-planar enclosures 110 are coupled to substrate 100 via an adhesive layer 120. A coating of a planarization layer 730 is then applied and cured. After curing planarization layer 730, a shadow mask can be loaded and used to transfer a patter to planarization layer 730 and non-planar enclosures 110. This can be followed by a wet strip of planarization layer 730 to separate non-planar enclosures 110 from substrate 100 and an adhesive layer 120.

In still other embodiments, laser direct imaging can be used in the fabrication process. For example, laser direct imaging can be used to project aperture patterns onto a substrate to be exposed. Laser direct imaging, as a maskless lithography technique, is different from laser drilling which is a direct writing technique, in that laser direct imaging only writes a computer designed pattern on a specific photosensitive thin film. Accordingly, laser direct imaging requires much less power than laser drilling and has much faster throughput.

Laser direct imaging can be accomplished with modifications to standard tools, including one wavelength for positioning, and one for exposure. While the current resolution is about 1-8 microns, it is believed this can be improved with smaller sample size.

In particular embodiments, the active agent can be loaded into the device by a method selected from the group consisting of capillary action, dipping, injecting, and pressure loading using positive or negative pressures. In certain embodiments, the one or more active agents comprise a solid (amorphous, co-crystals and crystalline), a liquid dosage, a semi-solid, a powder, or a hydrogel. In yet another aspect the device may optionally be attached to a medical device or a microelectronic circuit, where the microelectronic circuit comprises at least one of a sensor, a transmitter, a receiver, a transceiver, a switch, a power supply or a light and the medical device is selected from the group consisting of a stent, an urinary catheter, an intravascular catheter, a dialysis shunt, a wound drain tube, a skin suture, a vascular graft, an implantable mesh, an intraocular device, an eye buckle, a heart valve, and combinations and modifications thereof.

In certain embodiments, the shape of apertures may comprise a circle, ellipse, an oval, or a polygon. In specific embodiments, apertures may comprise circles with diameters ranging from 1 nanometer to 1 centimeter, 100 nanometers to 100 microns, 1 micron to 50 microns, 10 to 30 microns, 15 to 25 microns or 20 microns.

In particular embodiments, the one or more active agents may comprise drugs, proteins, vitamins, minerals, saccharides, lipids, nucleic acids, aptamers, miRNA, siRNA, peptides, manure, plant nutrients, chemicals, perfumes, fragrances, flavoring agents, animal feed, or effervescent gas releasing agents, and/or combinations and modifications thereof.

Certain embodiments provide for a method for treating a medical condition in a patient comprising the steps of identifying a patient exhibiting at least one symptom of the medical condition and implanting an active agent delivery device fabricated according to the methods disclosed herein. In exemplary embodiments, the active agent delivery device comprises a therapeutic agent supply capable of providing an effective dose for the medical condition symptom, wherein the delivery device releases the therapeutic agent with zero-order kinetics.

In one aspect the medical condition is selected from the group consisting of a cardiovascular disease, diabetes, epilepsy, Parkinson's disease, pain, cancer, ocular disease, and a fungal infection, wherein the cardiovascular disease is selected from the group consisting of stenosis, restenosis, late stent thrombosis, stroke, myocardial infarction, congestive heart disease, high blood pressure, angina, atherosclerosis or thrombosis. In certain embodiments, the diabetes is selected from the group consisting of type 1 diabetes, type 2 diabetes, juvenile diabetes, and gestational diabetes. In particular embodiments, the epilepsy is selected from the group consisting of generalized epilepsy, and partial epilepsy.

In specific embodiments, the pain condition may result from an anatomical site selected from the group consisting of abdomen, ankle, anal, back, bones, breast, ear, elbow, eye, finger, foot, groin, head, heel, hip, joints, knee, leg, muscles, neck, rib cage, shins, shoulder, flank, teeth, wrist or somatoform. The ocular disease may comprise macular degeneration, glaucoma, uveitis, retinitis, corneal ulcer or endophthalmitis in certain embodiments. In particular embodiments, the cancer is selected from the group comprising lung cancer, brain cancer, cervical cancer, uterine cancer, liver cancer, pancreatic cancer, leukemia, Hodgkin's lymphoma, Non-Hodgkin's lymphoma, kidney cancer, ovarian cancer, skin cancer, testicular cancer, and thyroid cancer. In certain embodiments, the fungal infection comprises a toenail infection or a fingernail infection.

Certain embodiments of the present invention relate to a medical device which acts as a housing containing drug reservoir, and means for facilitating release of drug from the drug reservoir to an anatomical site. In particular embodiments, the device enables a mechanism in which the drug is released at equal increments from the reservoir per unit time.

The device may be constructed such that the impermeable matrix material contains at least one passageway capable of releasing the encompassed drug wherein the ends of the device is plugged using a bioglue (i.e., for example, an albumin-glutaraldehyde composition). Alternatively, the device may be constructed such that the hollow core comprises an open end (i.e., for example, an outlet port) wherein the housing is devoid of passageways.

For better biocompatibility and biostability, which is a critical challenge to any implantable or injectable devices, the housing of the device may be made completely out of one biocompatible or biostable material and the wall of the housing is impermeable against bodily fluids except where passageways and/or outlet ports exist.

Material homogeneity is important for the robustness of the fabrication process and the long term biocompatibility and reliability of the final device. In certain prior devices, the channels or passageways are made out of a window part from a second material, different from the material of the housing of the drug depot. First, many additional fabrication steps will be needed for further assembly into a functional device. Second, interfaces between assembled parts are usually more susceptible to failure. Third, additional material qualification will be needed to ensure the biocompatibility and biostability of both materials used and the assembled device. These serious concerns and onerous qualification steps can greatly affect the progress of development and the time to market of a product.

The impermeable housing that encompasses a therapeutic agent supply with which the delivery device is made includes, but is not limited to, naturally occurring or synthetic materials that are biologically compatible with body fluids and tissues and are essentially insoluble and impermeable to the body fluid with which it will come in contact with. For example, these materials include, but are not limited to, glass, metal, ceramics, minerals, and polymers such as Titanium alloys and stainless steels, polyimides, polyamides, silicones, polyvinyl acetate, crosslinked polyvinyl alcohol, cross-linked polyvinyl butyrate, ethylene ethylacrylate, copolymer, polyethyl hexylacrylate, polyvinyl chloride, natural rubber, Teflon®, plasticized soft nylon, and silicone rubbers.

The passageways or channels can be perforations fabricated into and through the wall of the housing, connecting the drug supply in the hollow core with the bodily fluids outside of the housing. The material, the size and number, the surface chemistry and profile of the sidewall, of the passageways are all critical parameters that affect the gradual transport of drug molecules outside of the drug depot.

The shape of the one or more holes or perforations as described in the invention is selected from the group consisting of a triangle, a polygon, an undecagon, a trapezium or trapezoid, a quadrilateral, an icosagon, a star polygon, an annulus, a circle, a crescent, an ellipse, an oval, an arbelos, a Reuleaux triangle, a semicircle, a sphere, an Archimedean spiral, an astroid, a deltoid, a super ellipse, and a tomahawk.

The sidewall profile of the perforations can be vertical (e.g., the inclination angle of the sidewall with respect to the plane of the inner open is more or less a straight angle), tapered (e.g., the inclination angle is obtuse, much greater than 90 degrees) or retrograding (e.g., the inclination angle is acute, much smaller than 90 degrees). The inclination angle can affect the fluid dynamics involved in the delivery kinetics, but an important feature is the surface smoothness. Any protrusion or surface roughness can introduce variation in the release rate. Furthermore, protruding areas may become the trapping sites for molecules and raise the risk of clogging the dispensing channels.

The size and the number of passageways are nonetheless the main parameters affecting the delivery kinetics. The total dispensing cross-section of the passageways cannot be too big to drain the drug depot before the desired effective period of time. The size of each individual dispensing passageway, on the other hand, cannot be too small to be easily clogged by out-diffusion or outflow of the drug from the depot, or inward diffusion or flow of surrounding bodily fluids and its contents, such as cells and proteins, from the implant site. In many applications, for the example of circular holes or the perforations, the perforations are preferred to be in the order of micrometers, but the sidewall should have surface roughness in sub-micron or nanometer scale. This is where the innovative patterning technologies in embodiments the current invention differentiate from current micromachining approaches, such as laser drilling or ablation. The resulting perforations can range from 1 nanometers-1 centimeter, 100 nanometers-100 microns, 1 micron-50 microns, 10-30 microns, 15-25 microns or 20 microns in size, and with a smooth surface sidewall surface with surface roughness in a few percent of the perforation dimensions.

The size and shape of the whole device is also extremely important in the design of devices as it dictates the variety of anatomical sites where it can be placed. A macro-sized device may be suitable for implantation in or near vertebrae, but it may not be suitable for placement in an eye. Larger devices may also involve complex surgery both during implantation and removal. Furthermore, a larger device may also result in longer healing and recovery periods or device rejection by the body. Over the years, the dimensions of implantable drug delivery devices have decreased, and the duration of release has increased. These reductions in size has improved immunological responses, biocompatibility, and reduced side effects associated with earlier devices. Hence, there remains a need for drug delivery device which can be optimized to deliver any therapeutic, diagnostic, or prophylactic agent for any time period up to several years maintaining a controlled and desired rate.

In exemplary embodiments, the geometric shape of the housing can be arbitrarily regular or irregular. For convenience of fabrication, ease in placement and prevention of restenosis of the device, the housing usually assumes shapes with smooth surfaces and few to no sharp corners, such as cylinder, tube, sphere, and ellipsoids.

One embodiment of the proposed implantable drug delivery system is a tube made of biocompatible or biodegradable polymer with perforated dispensing holes fabricated with submicron resolution using an innovative micro- and nano-processing technology. It offers unique advantages over current drug delivery systems including, for example: (1) more capacity per implant for eliminating the polymeric core, such as EVA as in the case of Probuphine® (https://probuphine.com/wp-content/uploads/2017/06/final-approved-pi.pdf); (2) decoupled drug loading and depot fabrication process to allow more choices of medication; (3) better and more precise control over long term release by simply varying the geometric configurations of the device; (4) potential to package multiple medications into one enclosure and to dispense them at different rates; and (5) potential to integrate with biomarker sensors and control electronics for either better control over the drug release or better accommodation of individual differences. A zero-order release kinetics has been demonstrated in vitro on this platform with the release rate scalable with the number of the dispensing holes and the hole dimension. This control over the release rate offers a desirable platform to study the pharmacokinetics and pharmacodynamics in long term exposure.

In certain embodiments, the polymer tubes or other substrates where the micro-holes are formed can be integrated with microelectronics circuits and MEMS structures to form integrated devices for monitoring and controlled release of chemical agents or medications. In addition, more complex designs of delivery systems can be derived from the basic universal platform of an impermeable, biocompatible housing with micro-scale perforations as the dispensing passageways, and capable of zero-order delivery kinetics over an extended period of time. The designs can be expanded in the various aspects, as described more fully below.

Certain embodiments can include a multifunctional, multi-rate delivery system. Delivery of multiple therapeutic agents with different release rates can enable many innovative treatment regimens. For example, to mitigate the risk of accidental overdose, drug addiction treatment regimens may call for simultaneous release of buprenorphine and naloxone or naltrexone, but at various dose ratios. Certain types of cancer may be treated with multiple monoclonal antibodies (mAbs).

Such a multifunctional, multi-rate delivery system can be achieved with the basic platform in the invention. In one embodiment, the device may comprise a single housing, wherein the housing encompasses an agent supply comprising at least two therapeutic agents. In the embodiment of two agents, the device releases a first drug at a first release rate, but releases a second drug at a second release rate. Although it is not necessary to understand the mechanism of an invention, it is believed that the first and second agents are released at different rates because of differential solubility relative to the agent supply, different diffusivity and other flow dynamics parameters.

In another embodiment, the device may comprise at least two housings. In the embodiment of two bundled housings, the first housing comprises large diameter passageways and the second housing comprises small diameter passageways. The first housing encompasses a first agent supply that is released at a first rate and the second housing encompasses a second agent supply that is released at a second rate. Although it is not necessary to understand the mechanism of an invention, it is believed that the first agent is released at a faster rate than the second agent.

In another embodiment, the device may comprise one housing which contains at least two compartments. In the embodiment of one housing containing two compartments, the first compartment comprises a first therapeutic agent and the second compartment comprises a second therapeutic agent. The first compartment comprises large diameter passageways and the second compartment comprises small diameter passageways. Although it is not necessary to understand the mechanism of an invention, it is believed that the first agent in the first compartment is released at a first rate and the second agent in the first compartment is released at a second rate.

Still other aspects may include a resealable, replenishable device. In such embodiments, a biocompatible, but not biodegradable implanted device is naturally facing the challenge of retrieval of the device after exhaustion of the supply of the therapeutic agents or reaching the end of its useful life. Like for many other implantable devices, a retrieval procedure can be devised for the devices in the current invention. But to save the patient the pain and inconvenience of a retrieval procedure, the device can be made replenishable and resealable for a certain number of times. One embodiment of the current invention is to designate one area of the polymeric drug depot as the port for recharging the reservoir. In one embodiment, a sharp needle can be used to pierce the wall of the housing, reload the therapeutic agents, and the polymeric wall will reseal after the needle is retrieved. In another embodiment, a "flapper"-like valve with large area still attached to the rest of the polymeric housing can be fabricated into the wall. A needle can push open the flapper valve and release the therapeutic agent inside the depot housing. After retrieval of the needle, the hydraulic pressure pushes the flapper valve back in position. Depending on the design, though the valve is not perfectly sealed, the leakage through the flapper can be negligible in comparison with the target release rate. This resealable, replenishable valve design can also help maintain the sink condition for the zero-order delivery kinetics over further extended period of time.

Still other aspects may include a switchable device. In such embodiments, adding a switching mechanism, for example a remotely activatable switch, to the dispensing channel of the delivery device can greatly expand the application space by mitigating the risk of drug overdose or diversion and enabling tailored treatment regimens according to individual responses to the medication.

The switch can be built-in switches. In one embodiment, the device comprises an optional biodegradable polymer coating covering the perforations thereby preventing a release of the one or more active agents until the coating is removed, which then causes release of the one or more active agents. The biodegradable polymeric coating can be made of multiple layers and each layer covers different passageways. As the biodegradable layers dissolve in the bodily fluids, various passageways can be turned on at the desired timing or sequence.

These built-in switches can also be used to achieve a desired release rate with standard perforation patterns, which can lower the production cost. In one embodiment, plugging or blocking designated passageways with additional impermeable coating layer can be employed to adjust the release rate from devices with a standard perforation pattern.

Remotely activatable switches can be achieved by incorporating a Micro-Electrical-Mechanical-System (MEMS) switch that can be activated by means that pass through the human body, such as radio-frequency electromagnetic (EM) waves, infra-red light irradiation, or focused ultrasonic waves.

One feature of the invention comprises simplicity of design and prolonged duration drug release capability up to, and including, several years. Further, drug release may be unidirectional is not subject to back transfer or buildup of the drug as long as sink conditions are maintained. Although it is not necessary to understand the mechanism of an invention, it is believed that such a delivery device will eliminate the need for repeated dosing of a medicament thereby improving patient compliance. It is further believed that such a device would also decrease patient side effect risk, prolonged and unnecessary pain, and expense for many long term therapeutic regimens. In any drug treatment, it is desired to deliver a pharmaceutical agent directly at the targeted site for a sufficient duration in order to produce a required beneficial effect. Since the advent of time, man has sought means to find better cure. Oral, topical and inhalation are commonly used modes of drug administration. Modern era has witnessed development of alternate routes such as, systemic, intravitreal, and pulmonary delivery of drugs. However, age problems and disadvantages are associated with these conventional methods that restrict their effectiveness.

In most instances, drugs administered via these conventional routes result in the appearance of various deleterious side effects. For example, some drugs that are administered orally may not be properly absorbed through the stomach wall; may be degraded by the gastrointestinal tract; or may irritate the stomach causing an unwanted side effect. For example, insulin, which is a protein based drug, cannot be given orally since it would be degraded by proteolytic enzymes and therefore, must be given by injection. Further, Intravenous Ganciclovir (GCV) is effective in treatment of cytomegalovirus (CMV) retinitis in AIDS patients but 30-50% patients experience bone marrow toxicity resulting in neutropenia (neutrophil count <1000). Although an intravitreal administration of 200-400 µg/day of GCV twice a week has decreased the instances of neutropenia, this regimen requires repeated dosing thereby causing extreme discomfort to patients.

Some conventional routes of administration are problematic in maintaining a constant therapeutic level. For example, a drug concentration may either reach a toxic level or alternatively it may decrease as the drug is either metabolized (i.e., for example, by the liver) or eliminated (i.e., for example, by the kidney). Frequently, the drug levels may drop below the therapeutic levels and a second dose is needed.

One way to overcome this problem is to deliver drugs locally, that is, directly at the desired physiological site. A number of implantable drug delivery devices have been suggested to be capable of delivering a drug to a body lumen. One advantage of implanted drug delivery devices is related to local administration of a drug. Although it is not necessary to understand the mechanism of an invention, it is believed that local administration inherently improves efficacy and decreases side effects, as compared to other routes of administration such as oral, rectal, topical, or systemic. Nonetheless, one problem with the known implantable drug delivery devices is that the delivery rate cannot be controlled during all operational phases of the devices (i.e., for example, drug delivery rates may change thereby resulting in first order delivery kinetics or second order delivery kinetics).

Such problems result in a drug delivery device that administers drugs in an unpredictable pattern, thereby resulting in poor therapeutic benefit.

A zero order drug controlled release system offers many advantages, including for example: (1) drug levels are continuously maintained at a desirable therapeutic range; (2) adverse effects are reduced by targeting delivery to a specific site and avoiding distribution to unwanted tissues; (3) dose of drug is decreased while mean residence time is increased; (4) number of doses is decreased; (5) less invasive dosing decreases patient trauma and improves patient compliance; and (6) an inert and impermeable device protects the drug in the hostile environment.

Several implantable drug delivery systems have been reported which are capable of administering drugs at zero order rates. One of the earliest zero order devices was developed as an ocular insert as described in U.S. Pat. No. 3,618,604. The device was described as a sealed container having the drug in an anterior chamber. The device was capable of continuously releasing pilocarpine at a predetermined rate of 20-40 µg/hour for seven days for treating glaucoma. The ocular pressure level and pupil diameter were maintained throughout the 24-hour period of Ocusert placement. Nonetheless, as described in U.S. Pat. No. 4,014,335 certain problems have been identified with such devices such as the difficulty in sealing the margins to form a container. In addition, stresses and strains introduced into the membrane walls from deformation during manufacturing of the devices may cause the reservoir to rupture and leak.

Another such device, as described in U.S. Pat. No. 5,660,848 comprise a subdermal implant for uses as a contraceptive. This device was described as a central drug core; an intermediate polymeric layer controlling the rate of diffusion of drug; and the outer polymeric layer extending outwards from the intermediate layer. The device described in U.S. Pat. No. 5,660,848 does have problems. For example, the macroscopic size of the device releases significant amounts of the drug, progesterone, into the circulation causing problems of weight gain and vision loss in a small percentage of treated patients.

Osmotic minipumps have been reported as capable of providing zero-order drug release. One such device as described in U.S. Pat. No. 3,993,073 has a reservoir, which is formed of a drug carrier permeable to the passage of the drug and in which the drug has limited solubility. The wall is formed in at least a part of a drug release rate controlling material also permeable to the passage of the drug, but the rate of passage of the drug through the wall is lower than the rate passage of the drug through the drug carrier so that drug release by the wall is the drug release rate controlling step for releasing drug from the drug delivery device. Most of the osmotic pump devices are developed in form of a tablet or capsule, which can deliver drug up to a few hours or days and are not suitable for diseased conditions wherein, a constant amount of drug needs to be delivered for months and/or years.

Another minipump device, as described in U.S. Pat. Nos. 6,217,895 and 6,375, 972B1 comprises a sustained release device for the eye. This device is described as an inner core or reservoir including an effective agent; an impermeable tube which encloses the reservoir, at three sides; and a permeable membrane at the fourth side through which drug release takes place. The device is few hundred microns in dimensions and produces linear release. However, one drawback of the membrane based reservoir system is that the choice of the membrane is restricted by the solubility and diffusion coefficient of the drug. Consequently, a different membrane is required for each drug.

Three applications for exemplary embodiment disclosed herein include devices intended to treat aging and aging-related morbidities (e.g. extended release of immune suppressants), pancreatic cancer (e.g. micro-dosing over extended time period of chemotherapy drugs, such as ABRAXANE® (albumin-bound paclitaxel), GEMZAR® (gemcitabine), 5-FU (fluorouracil) and ONIVYDE® (irinotecan liposome injection)), and neurodegenerative diseases that affect brain functions (e.g. micro-dosing of therapeutic agents over extended time period at an implant site inside the brain to break the blood-brain barrier).

Inhibitors of mammalian Target of Rapamycin (mTOR, also known as mechanistic TOR), such as Rapamycin and its analogs (rapalog), have been widely investigated for their roles in controlling cell metabolism, and consequently treatment of various cancers and autoimmune diseases. Though broad health benefits in delaying the onset of many aging-related morbidities have been observed in low dose regimes of rapamycin or rapalog, severe side effects have also been reported due to long term suppression of immune system, improper regulation of mTORC1 (mammalian Target of Rapamycin Complex 1) and mTORC2 (mammalian Target of Rapamycin Complex 2) pathways. Control over the release of rapamycin or rapalogs over long time period and combination therapy with other drugs to mitigate the side effects become very critical for its pharmacokinetic and clinical studies. A combination therapy using Everolimus® (Rapalog: rapamycin analog) and exemestane (aromatase inhibitor) has been approved by the FDA to treat postmenopausal women with advanced hormone receptor-positive HER2-negative breast cancer.

The invention of the drug delivery system disclosed in this application can enable such studies and provide a convenient delivery platform for rapamycin or rapalogs and more complex combination treatment regimens. The hollow core can be filled with a supply of a composition or formulation containing at least rapamycin or variant mTOR inhibitors.

To achieve control over release rate at low dose levels, either the supply can be diluted or the orifices or perforations on the wall of the housing can be made rather small, in the order of micrometers, even to the submicron region. The number of perforations on the wall can offer a simple way of modulating the release rate at low dose levels.

To avoid excessive long term exposure to rapamycin or rapalogs, the device can be fitted with switches to shut off or open the perforations. One embodiment is to have the housing coated with a biodegradable coating that prevents release of the one or more active agents until the coating is dissolved in bodily fluids, which then causes release of the one or more active agents at a substantially constant rate.

The device can also be coated with a coating which comprises a remotely activatable switching mechanism that when not activated, prevents release of the one or more active agents, and causes release of the one or more active agents at a substantially constant rate when the mechanism is activated.

In another embodiment, the device comprises at least two biocompatible polyimide housings impermeable to the bodily fluids, with the first housing comprising a rapamycin or a rapalog and the second housing comprising another drug needed for combination therapy.

In another embodiment, the device comprises one biocompatible polyimide housing impermeable to the bodily fluids which further comprises at least two partitioned hollow cores with the first hollow core comprising a rapamycin or a rapalog and the second hollow core comprising another drug needed for combination therapy.

Pancreatic cancer is another area that we intend to apply the drug delivery platform disclosed in this application. It can be used for conventional chemotherapy and for the newly developed target therapies, such as growth factor inhibitors, anti-angiogenesis factors, targeting the cancer cells and drugs that target cancer stem cells, such as BBI-608 and demcizumab. One example is epidermal growth factor receptor (EGFR). Erlotinib (Tarceva), is already approved for use along with gemcitabine.

Other target cancer therapies include immune therapy, i.e., attempts to boost a person's immune system or give them ready-made components of an immune system to attack cancer cells. Examples of such immune therapies include injection of man-made monoclonal antibodies and drugs attacking immune system checkpoints. The monoclonal antibodies are proteins made to target a specific molecule, such as carcinoembryonic antigen (CEA), which is sometimes found on the surface of pancreatic cancer cells. Toxins or radioactive atoms can be attached to these antibodies to directly attack the tumor cells. Newer drugs that target the immune system checkpoints are expected to liberate the immune system from withholding its attack on the tumor cells. Challenges to delivering such new forms of therapies are that the efficacy will decrease significantly if allowed to go through digestive duct or other drug metabolism before reaching the target sites. The ideal route for administration would be direct implant in the proximity of or inside the tumorous organ.

With embodiments of the disclosed invention, the inventors can fabricate an implantable or injectable drug delivery system capable for controlled release over long periods of time for therapeutic agents to treat pancreatic cancers, comprising a biocompatible polyimide housing impermeable to the bodily fluids, a hollow core filled with supply of proper therapeutic agents, and one or more passageway(s) or channel(s) built into the otherwise impermeable wall of the housing. In specific embodiments, the periods of time include one hour to one day, one day to one week, one week to one month, one month to one year, or one year to ten years. To better control the release rate over the long term, the inner diameter of the passageways in the device is in the range of 0.1 µm-500 µm, 1-100 µm, 5-50 µm or 10-20 µm.

For the convenience of implanting this device in the proximity of or inside pancreas, the overall size of the device has to be miniaturized. For this purpose, the outer diameter of the housing is better to be controlled in the range of 50 µm-2000 µm, 500-1000 µm.

In one embodiment, the device can comprise a composition or formulation containing therapeutic agents for chemotherapy of pancreatic cancers, including ABRAXANE®

(albumin-bound paclitaxel), GEMZAR® (gemcitabine), 5-FU (fluorouracil) and ONIVYDE® (irinotecan liposome injection).

To enable the new therapies mentioned in the previous paragraphs, the device can be fabricated to deliver a drug from the new therapies, such as monoclonal antibodies, drugs targeting immune system checkpoints, or epidermal growth factor receptors, along with a more conventional chemotherapy, such as gemcitabine. To implement such combination therapies, the device can be made of multiple housings, or each housing can be partitioned into multiple compartments. In some cases, we may be able to use a simple one housing configuration, but rely on the different fluid dynamic properties of the drugs in a composition or formula stored in the hollow core to achieve different individual release rates for different drug components in the composition.

Optionally, the device can be coated with a biodegradable coating that prevents release of the one or more active agents until the coating is dissolved in bodily fluids, which then causes release of the one or more active agents at a substantially constant rate.

In another embodiment for the device to be used in treatment of pancreatic cancer, the device can be coated with a coating which comprises a remotely activatable switching mechanism that when not activated, prevents release of the one or more active agents, and causes release of the one or more active agents at a substantially constant rate when the mechanism is activated.

Due to limited diffusion and the presence of blood brain barrier, effective pharmacotherapy can be very difficult for diseased tissues or organs inside the brain. Even intercerebral implants have to be implanted in the proximity of the target tissue or organ to be effective. The potential of miniaturization of the disclosed drug delivery system and equipment with control electronics can open up more options for the implant sites.

The inventors will develop a miniature implantable or injectable drug delivery system capable for controlled release over long periods of time for therapeutic agents to be implanted into the brain for treatment of brain tumors, and neurodegenerative diseases, comprising a biocompatible polyimide housing impermeable to the bodily fluids, a hollow core filled with supply of the therapeutic agents, and one or more passageway(s) or channel(s) built into the otherwise impermeable wall of the housing. The housing can also be made from bio-dissolvable or biodegradable materials to avoid the need to retrieval after the depletion of the drug supply.

For long term drug release, the inner diameter of the passageways is in the range of 0.1 µm-500 µm, 1 µm-100 µm, or 1 µm-20 µm. For easy implant, the outer diameter of the housing is in the range of 20 µm-2000 µm, or 50 µm to 1000 µm.

To achieve control over the release onset time, the device can be coated with a biodegradable coating that prevents release of the one or more active agents until the coating is dissolved in bodily fluids, which then causes release of the one or more active agents at a substantially constant rate.

For even better external control, the device can be coated with a coating which comprises a remotely activatable switching mechanism that when not activated, prevents release of the one or more active agents, and causes release of the one or more active agents at a substantially constant rate when the mechanism is activated.

Examples

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Based on an innovative drug delivery concept consisting of a polymeric drug depot and micro-scale perforations as the dispensing channels [1-2], the inventors propose a plan to develop a drug delivery platform for controlled drug release over extended periods of time. Depending on the choice of medication, enclosure material and the dimensions of the depot and the perforations, drug delivery systems can be developed to meet some of the high-impact healthcare challenges of our time, such as chronic disease treatment, cancer treatment and HIV prevention.

This drug delivery system (DDS) offers significant advantages over other drug administration routes, including improved drug efficacy and patient compliance which are common benefits for implants. Moreover, the scalability of the release rates and overall device dimensions provides unprecedented opportunities for pharmacokinetic studies and innovative localized treatments.

Pharmacokinetic studies in vivo of a drug to define its absorption, distribution, and disposition are essential for FDA review and approval. The DDS can serve as a research platform to enable pharmacokinetic studies in vivo with better established dose conditions. With the DDS, drugs can be administered in multiple routes. Rarely can any route of drug administration achieve a long-term constant release rate into a target site. The potential capability of the DDS in delivering a drug, regardless of its physical and chemical properties, into a local site, bypassing the digestive tract, may provide an excellent test vehicle for pharmacokinetic studies in vivo with accuracy and efficiency. This can be very significant for the R&D in the pharmaceutical industry. It can be a good candidate for the "microdosing" devices mentioned in the cancer moonshot project. [5] With proper enclosure material and size miniaturization, the DDS can be implanted to study the usefulness of microdosing for longer periods of time to obtain initial information on pharmacokinetics, biodistribution, and specific tumor targeting of drugs, antibodies and other chemotherapy agents with the purpose of predicting efficacy of chemotherapy. This may help minimize adverse events at higher doses, and help the dosimetry calculations for PET imaging.

This DDS also holds great potentials in enabling novel drug treatments of various diseases, for example, for direct delivery to localized cancer lesions to treat pancreas and prostate cancer. The zero order rate of release delivery system can be loaded with gemcitabine for treatment of pancreatic cancer by piggy backing our device to a stent that can be placed in the bile duct to release gemcitabine or a combination of drugs for long periods of time. In the case of prostate cancer, we could localize our device in the prostate to deliver appropriate drugs effective for treating prostate cancer. The same approach could also be used to localize drugs in the brain.

In this proposal, due to budget and time constraints, we will demonstrate the capabilities of this delivery platform in a much simpler setup but with a profoundly important drug, rapamycin.

Rapamycin, a clinically proven mTOR inhibitor, has been widely investigated for its roles in delaying the onset of many aging-related diseases and consequently extending the healthy lifespan, the time span when a person stays healthy. [6-18] This can be very significant [19] as peace, improved living conditions, availability of quality healthcare and advancement of biomedical sciences all have contributed to ever increasing life expectancy in human society. Even as a relatively slow aging society in the developed world, the United States will still experience considerable growth in its older population between 2012 and 2050. In 2050, the population aged 65 and over is projected to be 83.7 million, almost double its estimated population of 43.1 million in 2012. [20] Coming with the aging population is the rise of noncommunicable diseases, such as heart diseases, cancer, and diabetes. Chronic diseases and disabilities are prevalent among the older population. The medication and long term care can have huge economic impact. Largely because of this demographic change, Medicare spending is projected to increase from $555 billion in 2011 to $903 billion in 2020, creating an inevitable fiscal crisis. [21, 22] Furthermore, complications in the elderly population due to poor medication compliance, and polypharmacy may be avoided using implants such as our DDS which is capable of delivering drugs for long periods of time at a constant rate.

The proposed study lays down the ground work for a novel drug delivery system (DDS) that enables innovative treatments of various diseases of great significance and importance to our society. The DDS fabricated with innovative semiconductor processing technologies that have distinct advantages over other implants in the following aspects:

a. Repeatable and reliable precise control over dimensions;

b. Potentials of device miniaturization; and c. Reduction of fabrication cost due to parallel processing.

In the future (Phase II if funded), we plan to develop a system-in-package approach to integrate this DDS with a biomarker sensor and an active driving element to form a smart, universal DDS. In addition, the capability of parallel processing of large quantity of tubes with high yield, tight quality control and cost reduction, as we have witnessed in the high volume manufacturing of microelectronics industry, offers a clear pathway for commercialization. This fabrication process shows significant advantages over the state-of-the-art laser drilling method.

The DDS is also innovative in its zero-order kinetics with a constant release rate for long times, which enables versatile applications in disease treatment as well as in its design and fabrication process. A zero-order release kinetics has been demonstrated in vitro on this platform with the release rate scalable with the number of the dispensing holes and the hole dimension. This control over the release rate offers an ideal platform to study the pharmacokinetics and pharmacodynamics in long term exposure.

The dosing strategy has been found critical in rapamycin inhibition of mTORC1 vs mTORC2 pathways. [23-25] The DDS offers an innovative administration route of rapamycin to enable various dosing strategies. Especially after the development of biodegradable delivery system and addition of a remotely controlled switch on the dispensing channels, we will be able to greatly reduce the intrusiveness of the technology.

The method of delivering low dose rapamycin over extended time periods is innovative too. This low dosage long term exposure can potentially suppress the severe side effects that have been reported in the literature, and pave the way for more scientific research work on this important drug which may holds key to understanding of tumor growth and cell aging. Compared with the current best known delivery method by inclusion of drug in the feed using encapsulation with an acrylic coating (Eudragit S100, Röhm Pharma, Germany) [18], the proposed DDS has great potential as a novel route for rapamycin administration to attain sufficiently high dose levels in the blood and to enable a more accurate study on its efficacy in healthy lifespan extension.

Figure 8:
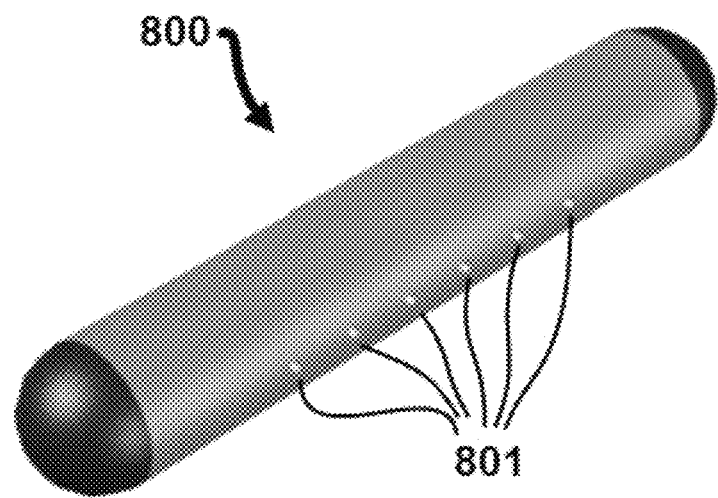
FIG. 8 illustrates a schematic of a implantable delivery system as disclosed herein.

Implantable drug delivery devices for long term drug release help overcome critical barriers facing maintenance treatments, especially those with antagonists, such as patient retention, low and variable bioavailability in oral or sublingual administration, and high drug cost. However, drug regulatory agencies around the world have been hesitant in giving them full approval, mostly due to lack of clinical data in long term treatments. In order to provide an understanding of the clinical responses of buprenorphine, naloxone or naltrexone release over a long period of time, the inventors propose a study on the pharmacokinetics, pharmacodynamics and behavior in rat models using an implantable delivery system 800 with apertures 801 as illustrated in FIG. 8 with the purpose of designing effective clinical and behavioral treatment of drug abuse.

Pharmacokinetics and pharmacodynamics have complementary roles in the clinical effectiveness of buprenorphine and naloxone or naltrexone combinations. Therapeutically, it is imperative to establish a dose-effect relationship to modulate the desired clinical response. Thus, the design of the dosing strategy is critical to assist the clinician in the behavioral treatment of drug abuse. The simplest and practical control of the response to buprenorphine and other medication is to control the blood plasma concentration.

However, the design of the dosing strategy (6 months to one-year delivery) requires an understanding of the pharmacokinetic and pharmacodynamics (PK-PD) response as a function of long periods of time. The goal is to achieve sufficient, but not excessive relevant blood plasma concentrations of the medication. It is not sufficient to understand the general PK-PD relationship of buprenorphine, but also the PK-PD characteristics, the delivery system, and the longtime release of the drugs in the user population. Understanding the mechanism of the PK-PD relationship after long exposure to the medication is essential prior to the development of treatment strategies of drug abuse patients.

The proposed implantable drug delivery system (IDDS) is a tube made of biocompatible or biodegradable polymer with perforated dispensing holes fabricated with submicron resolution using an innovative micro- and nano-processing technology. [ ] It offers unique advantages over current drug delivery systems in: 1) more capacity per implant for eliminating the polymeric core, such as EVA as in the case of Probuphine; 2) Decoupled drug loading and depot fabrication process to allow more choices of medication; 3) Better and more precise control over long term release by simply varying the geometric configurations of the device; 4) Potential to package multiple medications into one enclosure and to dispense them at different rates; and 5) Potential to integrate with biomarker sensors and control electronics for either better control over the drug release or better accommodation of individual differences. A zero-order release kinetics has been demonstrated in vitro on this platform with the release rate scalable with the number of the dispensing holes and the hole dimension. This control over the release rate offers an ideal platform to study the pharmacokinetics and pharmacodynamics in long term exposure.

The inventors have developed a process flow using semiconductor processing technologies [3] to make prototypes of the proposed perforated drug depot using polyimide tubing with various inner diameters (Microlumen, FL, USA). A typical process flow is presented in FIG. 9. It is based on photo-lithography and reactive ion etching technologies as shown in steps 901-907. A polyimide tube 908 is inserted as shown. The inventors expect even better dimensional control and edge smoothness to be achieved with industrial grade wafer processing equipment in the future. The inventors have demonstrated the capability of making holes of different sizes ranging from 10 µm to 300 µm or larger.

Figure 9:
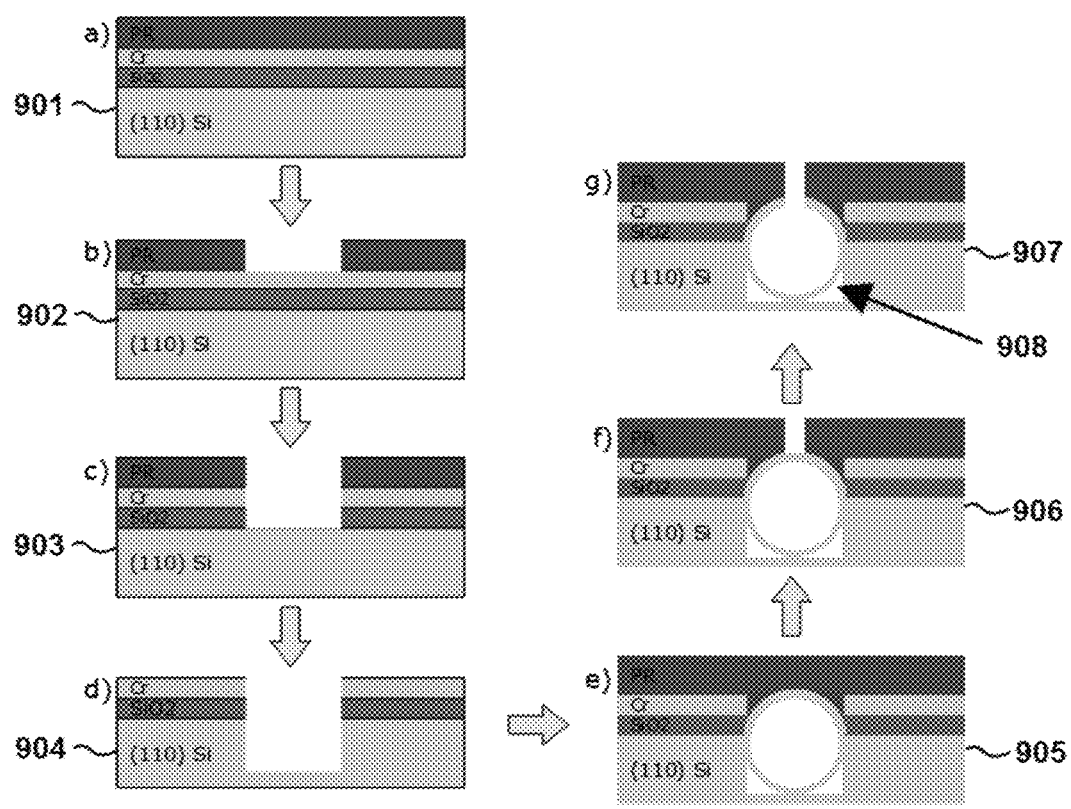
FIG. 9 illustrates an exemplary embodiment of a system and method as disclosed herein
Figure 10:
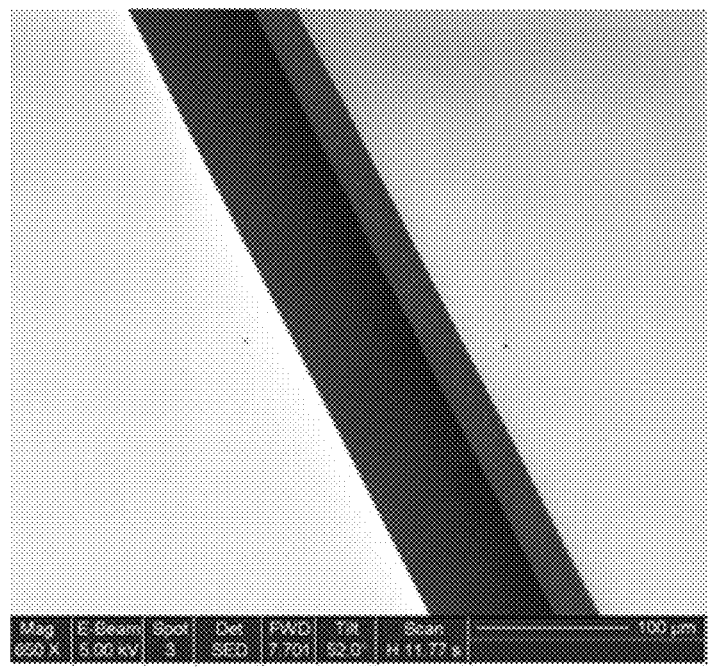
FIG. 10 illustrates a detailed view of a feature of the embodiment of FIG. 9.
Figure 10:
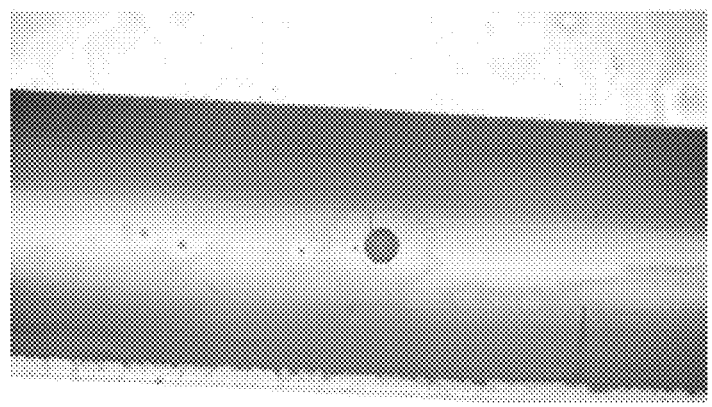
Figure 11:
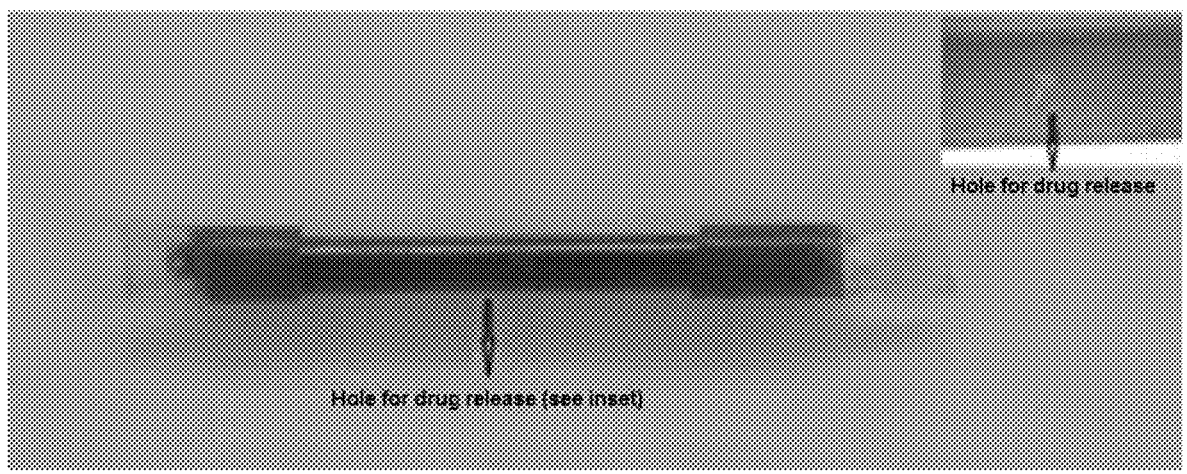
FIG. 11 illustrates a photograph of an exemplary embodiment as disclosed herein.

FIG. 10 provides a close-up view of the silicon trench and orifice formed in the tube during the process shown in FIG. 9. Using this fabrication process flow, the inventors were able to make a prototype of the drug delivery systems. FIG. 11 provides a photograph of a prototype implantable delivery system 900 that is approximately 200 mm in length and 1.8 mm in diameter. System 900 comprises an aperture 901 that is approximately 200 microns in diameter.

Figure 12:
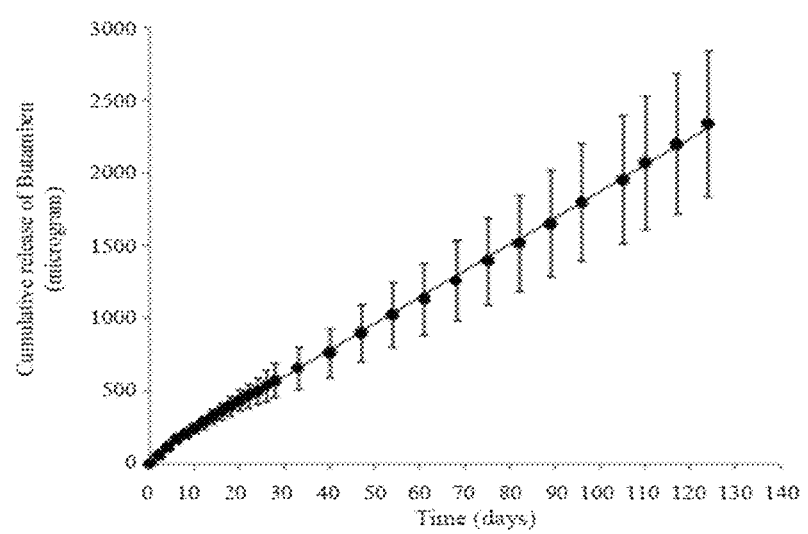
FIG. 12 illustrates a graph of a release rate of butamben from an exemplary embodiment as disclosed herein.

The perforated tubes of system 900 shown in FIG. 11 were then packed aseptically with the model drug butamben powder (Sigma Aldrich, MO, USA) and the ends sealed with octyl-cyanoacrylate (liquid Band-Aid). Twelve tubes were loaded and placed in a micro-vial containing 1.8 ml of phosphate-buffered saline (PBS). Non-perforated polyimide tubes were used as control in the study. The micro-vials were placed in a rocker (46-48 oscillations/min) and maintained inside an incubator (37° C.+/−1.0° C.) for the entire duration. Samples were collected as a function of time for 120 days and the volume of the samples replenished with fresh PBS. FIG. 12 shows the preliminary release of butamben approximating zero-order release at a constant rate beyond 120 days (N=12+/−Std. Dev.). The slope represents the rate of release.

Figure 13:
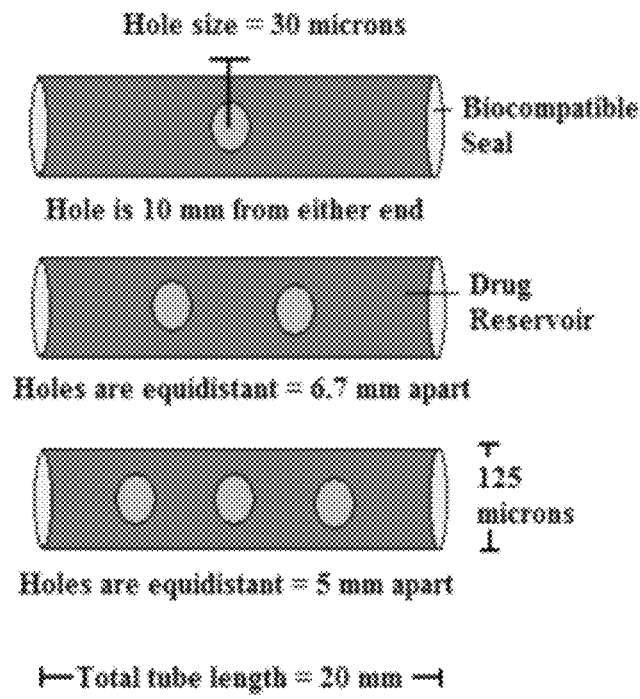
FIG. 13 illustrates a schematic of exemplary embodiments as disclosed herein with different numbers of apertures.
Figure 14:
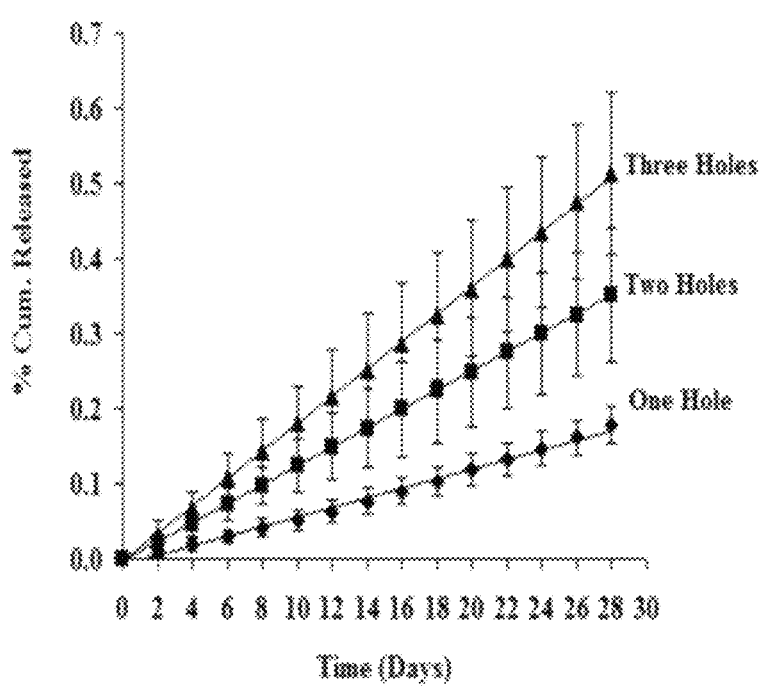
FIG. 14 illustrates a graph of a release rate of Crystal violet from exemplary embodiments as disclosed herein.
Figure 15:
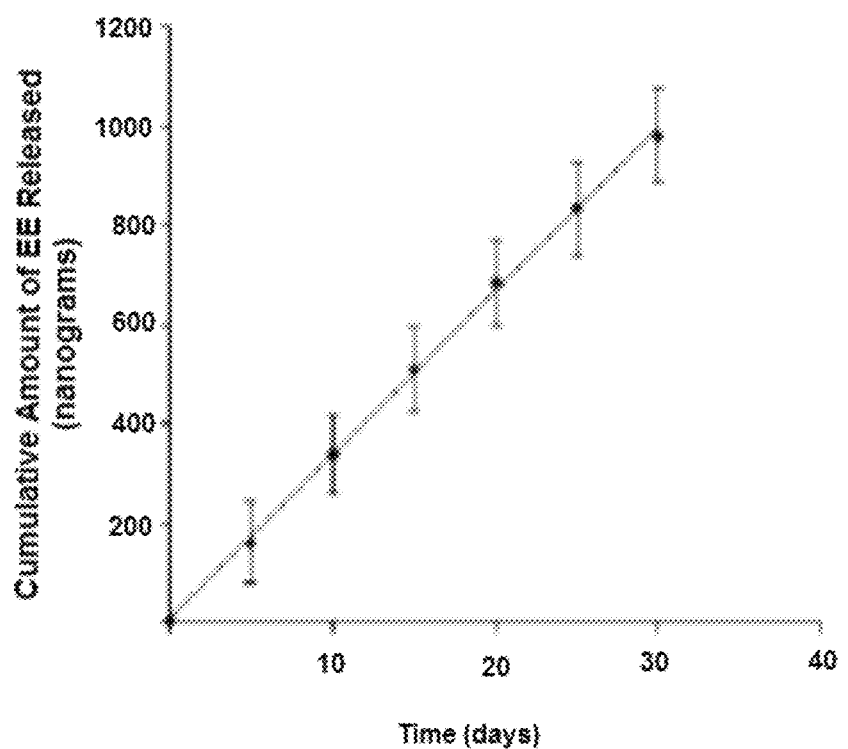
FIG. 15 illustrates a graph of a release rate of ethinyl estradiol from an exemplary embodiment as disclosed herein.

The inventors further demonstrated a long term zero-order release behavior with multiple hole patterns as shown in FIG. 13. In FIG. 13, a schematic is shown of polyimide tubes with different number of holes on the surface. The holes are equidistant from each other and also from the ends of the tube. FIG. 14 illustrates the release of crystal violet from devices into phosphate buffered saline. The rate of release is a function of the solubility of the drug and size of the hole across which diffusion occurs. The release profile of Crystal violet, a hydrophilic compound, from the three subsets is shown. Each curve represents twelve tubes. Data is presented as a mean with standard deviation. FIG. 15 illustrates the release of ethinyl estradiol, a hydrophobic drug over a 30 day period from a 20 micron perforation. The cumulative release of ethinyl estradiol (EE) from the 20 micron group over 30 days is shown. The release profile exhibits a zero order kinetics with R2=0.9990. The slope of the line suggests the rate of EE release of 32.7±7.3 ng/day. Data is presented as a mean with standard deviation, n=6.

The concept of this DDS was also validated in a preliminary in vivo test to demonstrate its capability of long-term release at a constant rate of hydrophilic drugs. Sodium fluorescein mixed with stearic acid was used as a model drug. Micro-perforated polyimide microtubes with inside diameter 1.8 mm, tube length 20 mm, hole size 0.15 mm were used in the study.

Figure 16:
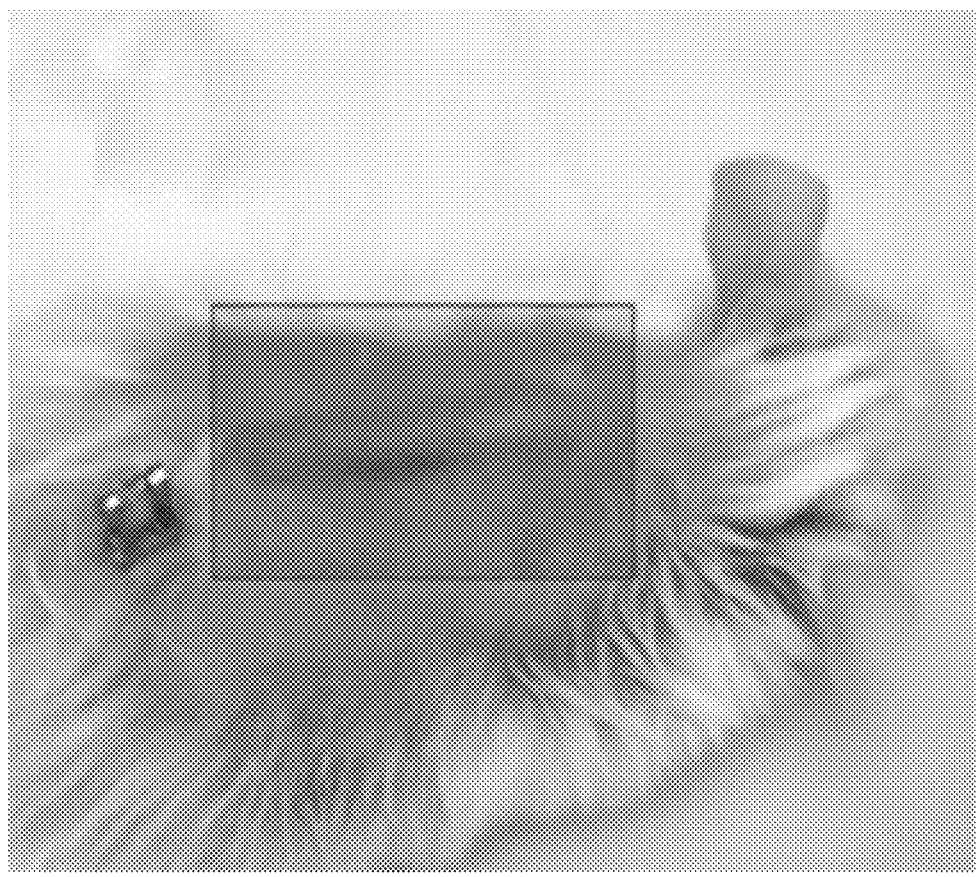
FIG. 16 illustrates a photograph of an exemplary embodiments subcutaneously implanted.

Results as shown in FIG. 16 indicated no clinical adverse reaction at the site of device implantation specific to the device and that the DDS was found to be biocompatible and capable of long-term constant release of a hydrophilic drug such as sodium fluorescein.

The concept of this DDS was also validated in a preliminary in vivo test to demonstrate its capability of long-term release at a constant rate of hydrophilic drugs. Sodium fluorescein mixed with stearic acid was used as a model drug. Micro-perforated polyimide microtubes with inside diameter 1.8 mm, tube length 20 mm, hole size 0.15 mm were used in the study.

Figure 17:
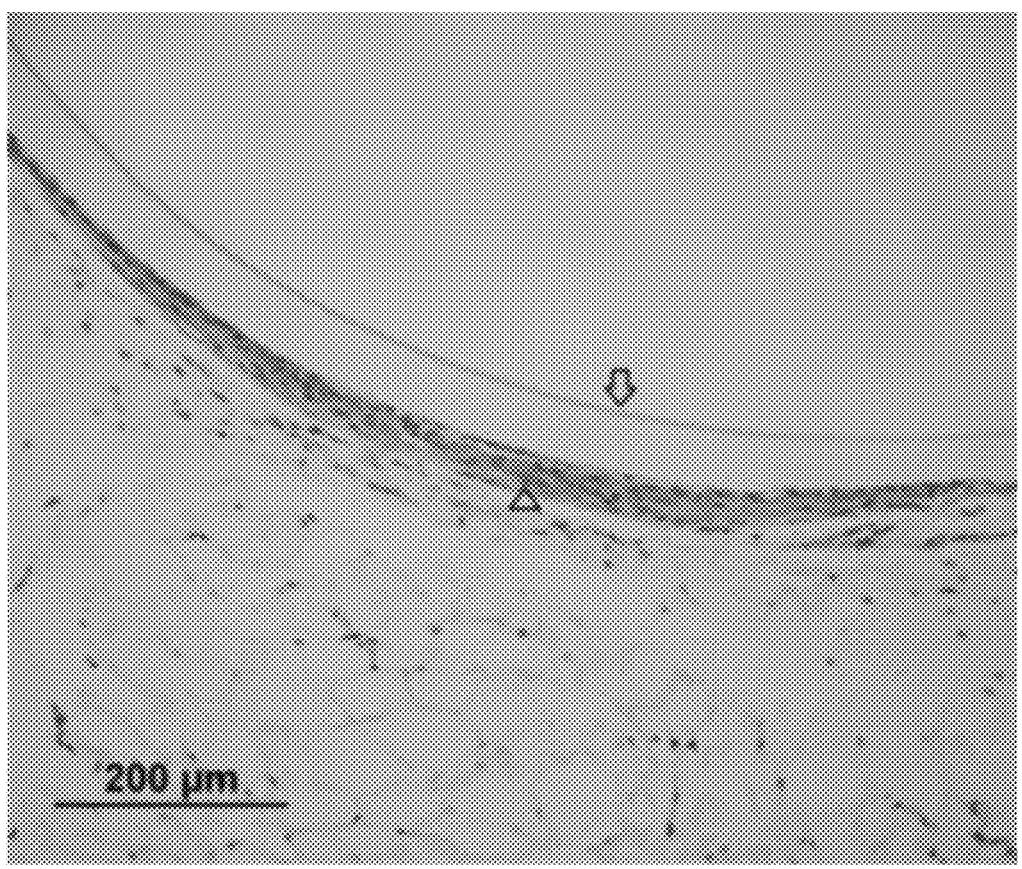
FIG. 17 illustrates an image of the implantation site of FIG. 16.
Figure 18:
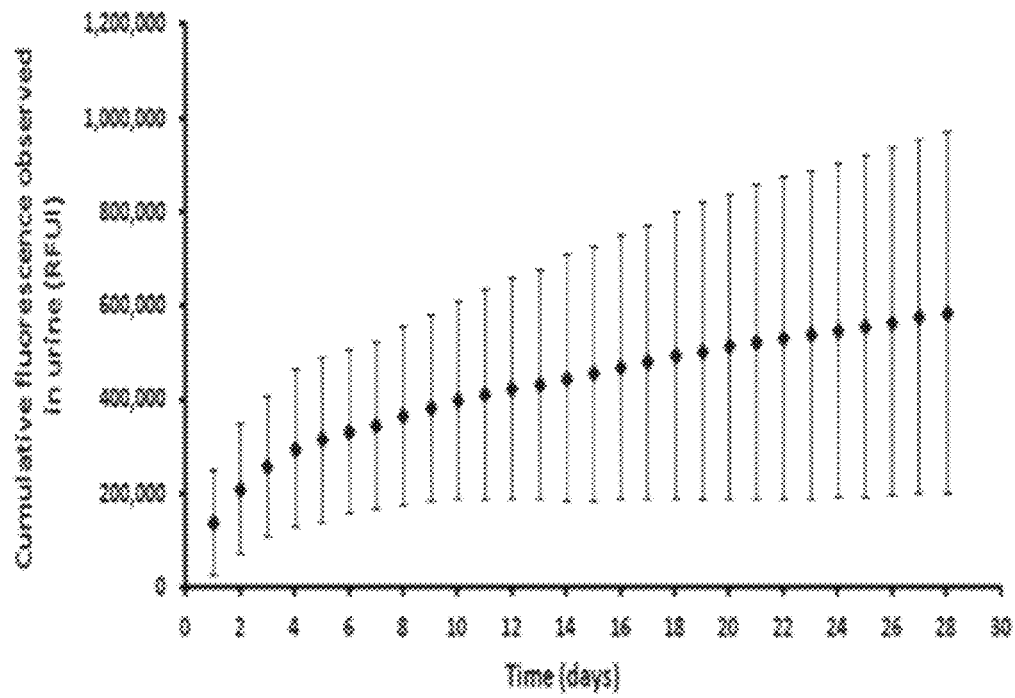
FIG. 18 illustrates a graph of the cumulative appearance of fluorescence in urine from the subject of implantation in FIG. 16.

Results as shown in FIGS. 16-18 indicate no clinical adverse reaction at the site of device implantation specific to the device and that the DDS was found to be biocompatible and capable of long-term constant release of a hydrophilic drug such as sodium fluorescein.

FIG. 16 shows the subcutaneously implanted tube at 3 months. FIG. 17 illustrates fibroblasts, collagen, and rare inflammatory cells (indicated by arrow head) were observed surrounding the polyimide tube (indicated by arrow). FIG. 18 shows the cumulative appearance of fluorescence in urine after implantation of the perforated polyimide DDS containing a 40:60 mixture of fluorescein/stearic acid. Each point represents as mean with standard deviation (n=7).

Figure 19:
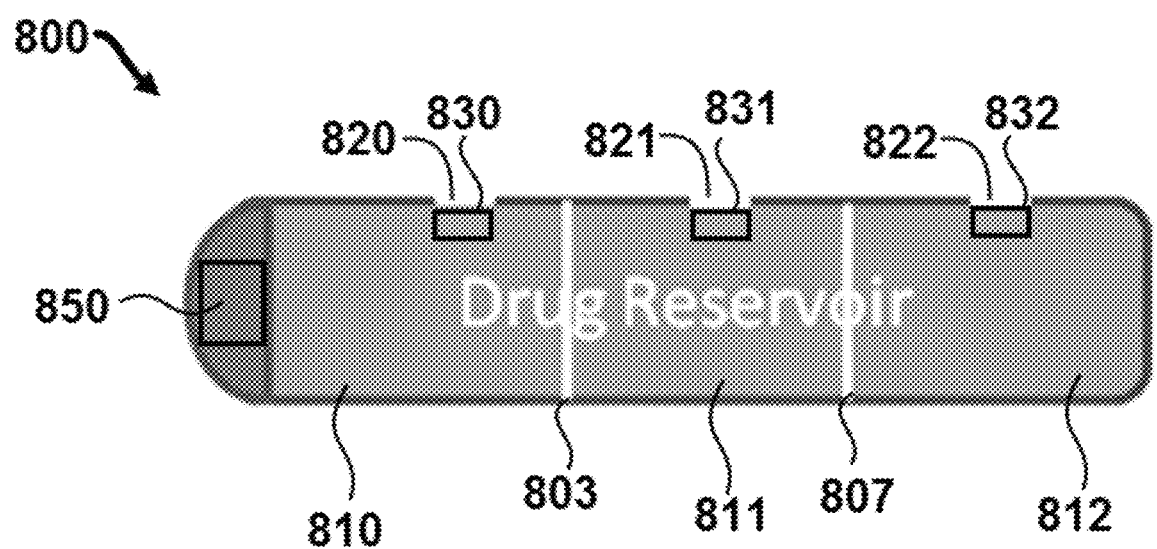
FIG. 19 illustrates a schematic of an exemplary embodiment of a device as disclosed herein.

As disclosed herein, embodiments of the present invention disclose configurations of a drug delivery system intended for long-term controlled drug release. As shown in FIG. 19, significant novel features of device 800 include: multiple chambers 810, 811 and 812 (separated by partitions 803 and 807) to deliver multiple drugs with individual dispensing aperture 820, 821 and 822 externally activatable switches 830, 831 and 834 on each dispensing aperture 820-822, control electronics 850 comprising, for example, biomarker sensors, electrically activated valves, and micropumps to regulate the release rates. The enclosure can be made of biocompatible or biodegradable materials and may be of varying wall thickness to allow delivery at different time.

All of the devices, systems and/or methods disclosed and claimed herein can be made and executed without undue experimentation in light of the present disclosure. While the devices, systems and methods of this invention have been described in terms of particular embodiments, it will be apparent to those of skill in the art that variations may be applied to the devices, systems and/or methods in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The contents of the following references are incorporated by reference herein:
U.S. Pat. No. 3,854,480
U.S. Pat. No. 3,948,254
U.S. Pat. No. 4,014,355
U.S. Pat. No. 4,260,736
U.S. Pat. No. 4,283,394
U.S. Pat. No. 5,378,475
U.S. Pat. No. 6,051,576
U.S. Pat. No. 6,039,975
U.S. Pat. No. 5,935,597
U.S. Pat. No. 5,989,581
U.S. Pat. No. 5,902,598
U.S. Pat. No. 9,005,649
US20040009222
US20120130300
US20120177716

The invention claimed is:

1. A method of making a device for delivery of one or more active agents with short or long zero-order release kinetics, the method comprising:
   providing a substrate, and a plurality of non-planar enclosures, wherein the substrate comprises a first side and a second side;
   coupling the plurality of non-planar enclosures to the first side of the substrate;
   fabricating a plurality of apertures in the plurality of non-planar enclosures, wherein the plurality of apertures are fabricated via a maskless fabrication process; and
   loading the one or more active agents in the plurality of non-planar enclosures.

2. The method of claim 1 further comprising separating the plurality of non-planar enclosures from the substrate.

3. The method of claim 1 wherein each of the plurality of non-planar enclosures comprises an interior cavity and at least one open end, and wherein loading the one or more active agents in the plurality of non-planar enclosures comprises:
   placing the one or more active agents in the interior cavity via the open end; and
   sealing the open end of the interior cavity.

4. The method of claim 1 where the plurality of non-planar enclosures are positioned on the first side of the substrate using an adhesive layer, a molding layer or a combination of both, wherein the adhesive layer comprises a tape with an adhesive first side and an adhesive second side and wherein the molding layer is a pattern definition layer in the maskless lithography process.

5. The method of claim 4 wherein the maskless lithography process is an e-beam resist process or photoresist process.

6. The method of claim 1 where the maskless fabrication process utilizes a computer programmed and controlled focused ion beam or multiple focused ion beams to fabricate the plurality of apertures in the plurality of non-planar enclosures without using a pattern definition and transfer process, wherein the ion beam is made of biocompatible and reactive ions.

7. The method of claim 6 where the ion beam is made of oxygen ions or hydrogen ions.

8. The method of claim 1 where the maskless fabrication process utilizes a pattern definition and transfer process comprising:
   depositing a pattern definition layer on the plurality of non-planar enclosures;
   forming patterns of the apertures in the pattern definition layer using a maskless lithography process; and
   transferring the patterns into the plurality of non-planar enclosures using an etch process, where the maskless lithography process utilizes a computer programmed and controlled single electron beam or multiple electron beams.

9. The method of claim 8 wherein the maskless fabrication process comprises forming apertures in a pattern transfer layer before transferring an aperture pattern into the plurality of enclosures and wherein the pattern transfer layer is a biocompatible dielectric pattern transfer layer.

10. The method of claim 9 wherein the biocompatible dielectric pattern transfer layer is a spin on glass pattern transfer layer or an amorphous carbon pattern transfer layer.

11. The method of claim 1 where the maskless lithography process utilizes laser direct imaging, where the pattern to be imaged is programmed on a computer and projected with controlled light beam or beams.

12. The method of claim 1 wherein the plurality of non-planar enclosures comprises a plurality of tubular enclosures.

13. The method of claim 1 wherein the plurality of non-planar enclosures comprises a plurality of spherical enclosures.

14. The method of claim 1 wherein the substrate is a silicon wafer.

15. The method of claim 14 wherein the maskless fabrication process comprises forming apertures in a pattern transfer layer before transferring the aperture patterns into the plurality of enclosures and the pattern transfer layer is a biocompatible metal pattern transfer layer or a titanium layer.

16. The method of claim 15 wherein the maskless fabrication process utilizes a release layer.

17. The method of claim 14 wherein an aperture pattern are formed with direct writing processes utilizing an electron beam, ion beam, or laser beam.

18. The method of claim 1 wherein the plurality of non-planar enclosures comprises tubular polyimide structures.

* * * * *